US010561474B2

(12) United States Patent
Adams et al.

(10) Patent No.: US 10,561,474 B2
(45) Date of Patent: Feb. 18, 2020

(54) SURGICAL STAPLER WITH END OF STROKE INDICATOR

(71) Applicant: Ethicon Endo-Surgery, LLC, Guaynabo, PR (US)

(72) Inventors: Thomas Adams, Cincinnati, OH (US); Barry T. Jamison, Fairfield, OH (US); Steven Dickinson, Cincinnati, OH (US); Anil K. Nalagatla, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 374 days.

(21) Appl. No.: 14/985,541

(22) Filed: Dec. 31, 2015

(65) Prior Publication Data

US 2017/0189132 A1 Jul. 6, 2017

(51) Int. Cl.
*A61B 90/00* (2016.01)
*A61B 17/068* (2006.01)
*A61B 17/072* (2006.01)

(52) U.S. Cl.
CPC .......... *A61B 90/08* (2016.02); *A61B 17/0686* (2013.01); *A61B 17/072* (2013.01);
(Continued)

(58) Field of Classification Search
CPC .......... A61B 2017/07221; A61B 2017/07228; A61B 2017/07271; A61B 2017/07285;
(Continued)

(56) References Cited

U.S. PATENT DOCUMENTS

| 3,494,533 A | 2/1970 | Green et al. |
| 3,795,034 A | 3/1974 | Strekopytov et al. |

(Continued)

FOREIGN PATENT DOCUMENTS

| CN | 201 445 537 U | 5/2010 |
| CN | 103 083 053 A | 5/2013 |

(Continued)

OTHER PUBLICATIONS

U.S. Appl. No. 12/031,573, filed Feb. 14, 2008.
(Continued)

*Primary Examiner* — Todd J Scherbel
*Assistant Examiner* — Brooke Labranche
(74) *Attorney, Agent, or Firm* — Frost Brown Todd LLC

(57) ABSTRACT

A surgical instrument and method for indicating that a cartridge has been fired includes an end effector receiving a cartridge having at least one of a knife and a plurality of staples, a shaft assembly connected to the end effector, and a handle assembly. The handle assembly has a handle housing, a firing member configured to selectively actuate from a first position to a second position as a firing stroke, and a feedback generator operatively connected to the firing member. The firing member is configured to actuate the cartridge from an unfired cartridge position to a fired cartridge position when the firing member is actuated. The feedback generator is configured to communicate an audible sound and a visual indicia to an operator indicative of the firing member completing the firing stroke for actuating the cartridge to the fired cartridge position.

20 Claims, 34 Drawing Sheets

(52) U.S. Cl.
CPC ............. *A61B 2017/07221* (2013.01); *A61B 2017/07228* (2013.01); *A61B 2017/07271* (2013.01); *A61B 2017/07285* (2013.01); *A61B 2090/0811* (2016.02)

(58) Field of Classification Search
CPC ............ A61B 2017/2945; A61B 90/08; A61B 17/0686; A61B 17/072; A61B 2090/0811; A61B 2017/0038
See application file for complete search history.

(56) References Cited

U.S. PATENT DOCUMENTS

| | | |
|---|---|---|
| 4,047,654 A | 9/1977 | Alvarado |
| 4,216,891 A | 8/1980 | Behlke |
| 4,568,009 A | 2/1986 | Green |
| 4,580,712 A | 4/1986 | Green |
| 4,607,636 A | 8/1986 | Kula et al. |
| 4,767,044 A | 8/1988 | Green |
| 4,802,614 A | 2/1989 | Green et al. |
| 5,071,052 A | 12/1991 | Rodak et al. |
| 5,403,312 A | 4/1995 | Yates et al. |
| 5,673,842 A | 10/1997 | Bittner et al. |
| 6,817,508 B1 | 11/2004 | Racenet et al. |
| 6,988,650 B2 | 1/2006 | Schwemberger et al. |
| 7,000,818 B2 | 2/2006 | Shelton et al. |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,407,076 B2 | 8/2008 | Racenet et al. |
| 7,422,139 B2 | 9/2008 | Shelton et al. |
| 7,464,849 B2 | 12/2008 | Shelton et al. |
| 7,670,334 B2 | 3/2010 | Hueil et al. |
| 7,753,245 B2 | 7/2010 | Boudreaux et al. |
| 7,845,537 B2 | 12/2010 | Shelton et al. |
| 7,913,891 B2 * | 3/2011 | Doll ................ A61B 17/07207 227/175.2 |
| 7,980,443 B2 | 7/2011 | Scheib et al. |
| 8,210,411 B2 | 7/2012 | Yates et al. |
| 8,308,040 B2 | 11/2012 | Huang et al. |
| 8,317,070 B2 | 11/2012 | Hueil et al. |
| 8,220,688 B2 | 12/2012 | Laurent et al. |
| 8,353,436 B2 | 1/2013 | Kasvikis |
| 8,371,494 B2 | 2/2013 | Racenet et al. |
| 8,393,514 B2 | 3/2013 | Shelton et al. |
| 8,561,870 B2 | 10/2013 | Baxter et al. |
| 8,579,178 B2 | 11/2013 | Holsten et al. |
| 8,608,045 B2 | 12/2013 | Smith et al. |
| 8,733,613 B2 | 5/2014 | Huitema et al. |
| 9,072,535 B2 | 7/2015 | Shelton et al. |
| 9,101,358 B2 | 8/2015 | Kerr et al. |
| 9,198,658 B2 | 12/2015 | Kasvikis |
| 9,566,066 B2 | 2/2017 | Kasvikis |
| 9,700,316 B2 | 7/2017 | Mohan et al. |
| 9,814,460 B2 | 11/2017 | Kimsey et al. |
| 10,045,780 B2 | 8/2018 | Adams et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2005/0247753 A1 | 11/2005 | Kelly et al. |
| 2007/0093856 A1* | 4/2007 | Whitfield ........... A61B 17/1285 606/142 |
| 2007/0175955 A1 | 8/2007 | Shelton et al. |
| 2011/0155782 A1* | 6/2011 | Natarajan ............ A61B 17/072 227/176.1 |
| 2013/0334284 A1 | 12/2013 | Swayze et al. |
| 2014/0263551 A1 | 9/2014 | Hall et al. |
| 2014/0263552 A1 | 9/2014 | Hall et al. |
| 2015/0053748 A1* | 2/2015 | Yates .................... G16H 40/63 227/180.1 |
| 2015/0196347 A1 | 7/2015 | Yates et al. |
| 2017/0189012 A1 | 7/2017 | Adams et al. |
| 2017/0189015 A1 | 7/2017 | Adams et al. |
| 2017/0189021 A1 | 7/2017 | Kimsey et al. |
| 2017/0189024 A1 | 7/2017 | Adams et al. |

FOREIGN PATENT DOCUMENTS

| | | |
|---|---|---|
| CN | 102 895 010 B | 12/2014 |
| EP | 0 246 870 A2 | 11/1987 |
| EP | 1 550 407 A2 | 7/2005 |
| EP | 1 550 410 A2 | 7/2005 |
| EP | 1 550 414 A2 | 7/2005 |
| EP | 1 723 914 A1 | 11/2006 |
| EP | 1 997 439 A2 | 12/2008 |
| EP | 2 090 255 A1 | 8/2009 |
| EP | 2 165 653 A2 | 3/2010 |
| EP | 2 248 474 A2 | 11/2010 |
| EP | 2 839 790 A1 | 2/2015 |
| WO | WO 86/02254 A1 | 4/1986 |
| WO | WO 2015/153340 A2 | 10/2015 |

OTHER PUBLICATIONS

U.S. Appl. No. 14/813,242, filed Jul. 30, 2015.
European Search Report and Written Opinion dated Feb. 22, 2017 for Application No. EP 16207604.6, 11 pgs.
European Search Report and Written Opinion dated Mar. 23, 2017 for Application No. EP 16207608.7, 10 pgs.
European Search Report, Partial, and Written Opinion dated Sep. 14, 2017 for Application No. EP 16207536.0, 11 pgs.
European Search Report and Written Opinion dated Mar. 16, 2017 for Application No. EP 16207619.4, 9 pgs.
European Examination Report dated Jun. 15, 2018 for Application No. EP 16207619.4, 3 pgs.
European Search Report and Written Opinion dated Mar. 13, 2017 for Application No. EP 16207527.9, 7 pgs.
International Search Report and Written Opinion dated Mar. 7, 2017 for Application No. PCT/US2016/066293, 15 pgs.
International Search Report and Written Opinion dated Mar. 23, 2017 for Application No. PCT/US2016/066802, 16 pgs.
International Search Report and Written Opinion dated Jun. 16, 2017 for Application No. PCT/US2016/067429, 13 pgs.
International Search Report and Written Opinion dated Mar. 17, 2017 for Application No. PCT/US2016/067433, 15 pgs.
International Search Report and Written Opinion dated Mar. 13, 2017 for Application No. PCT/US2016/067436, 12 pgs.
U.S. Appl. No. 16/029,893, filed Jul. 9, 2018.

* cited by examiner

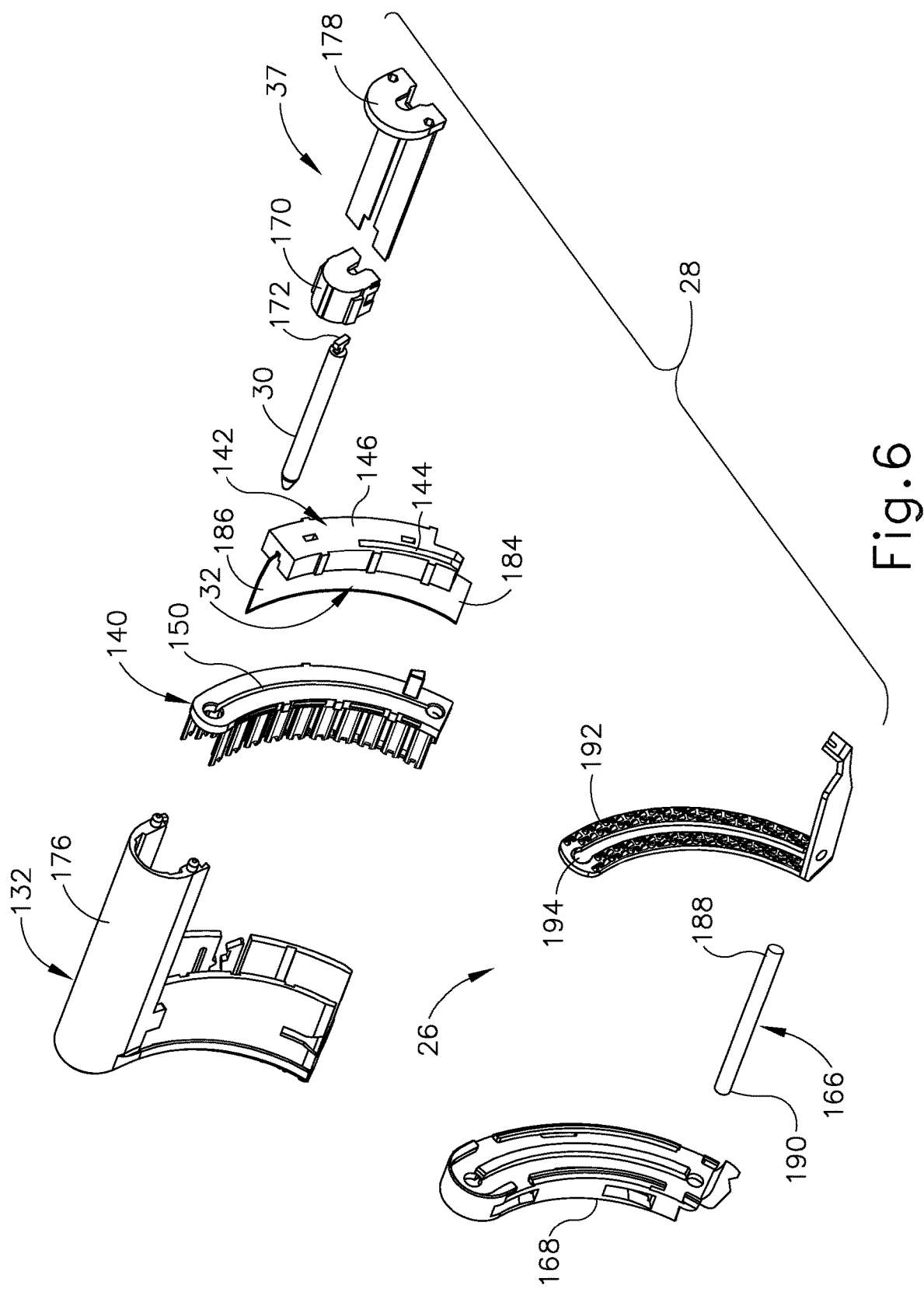

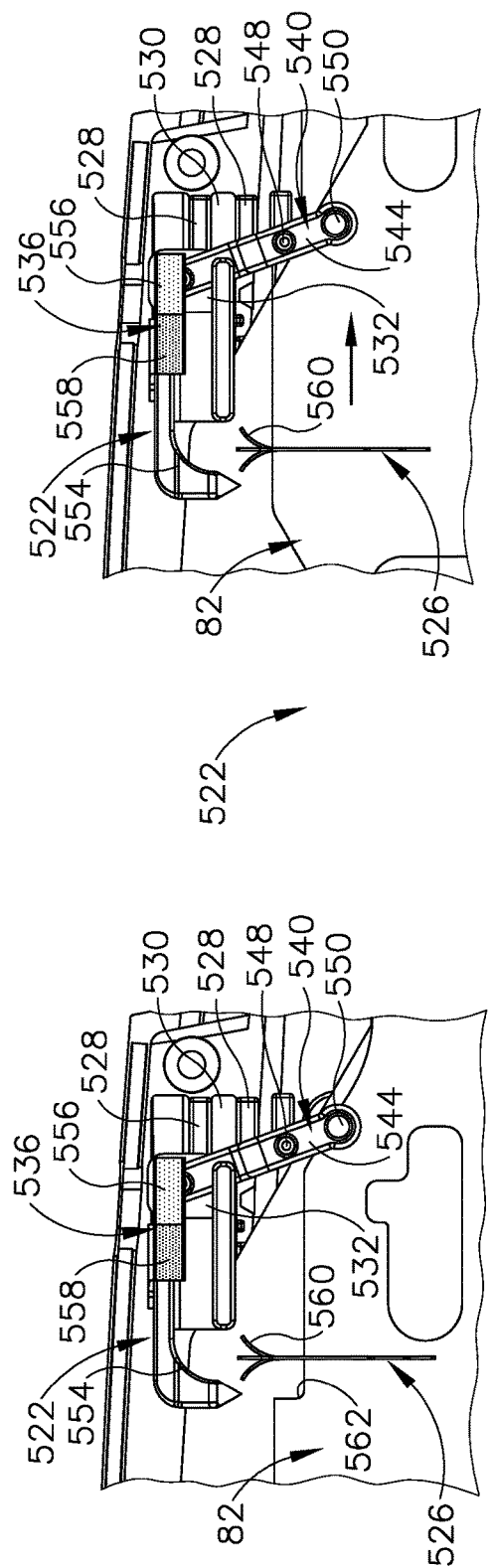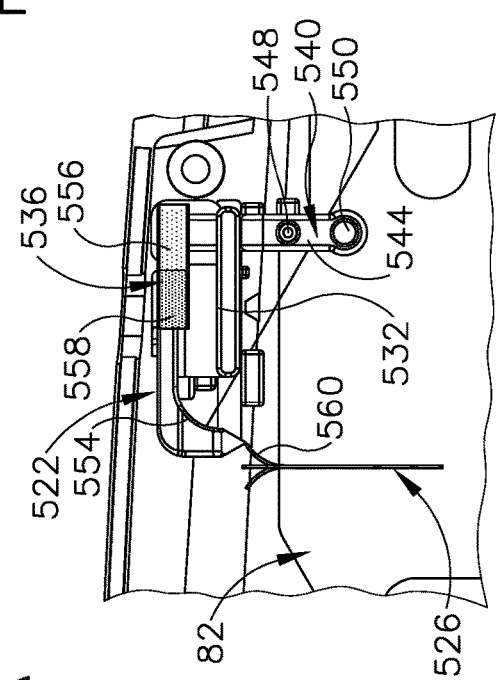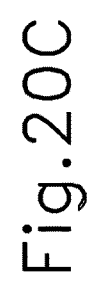

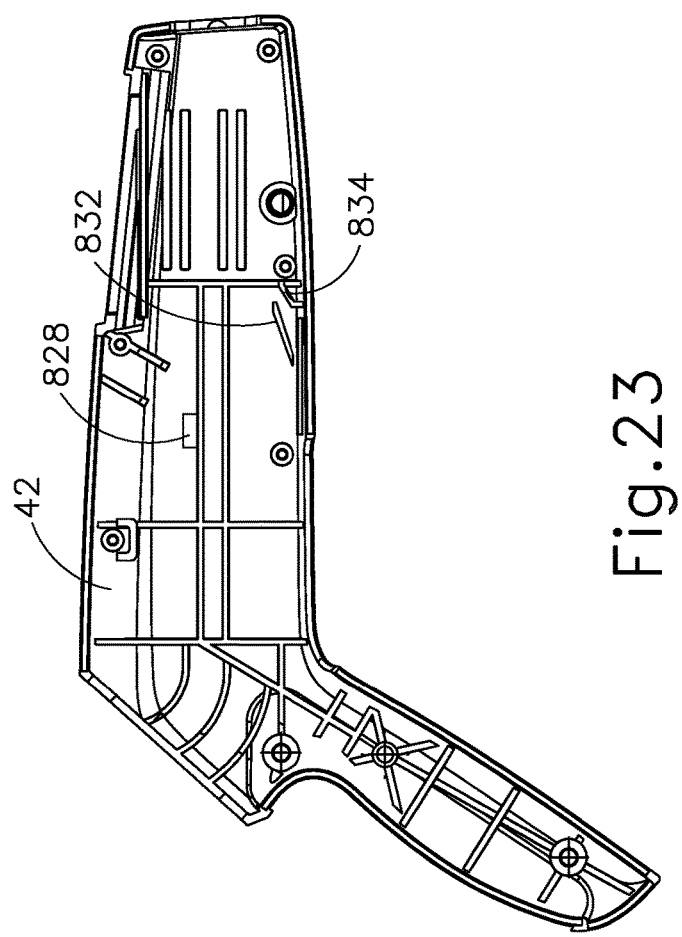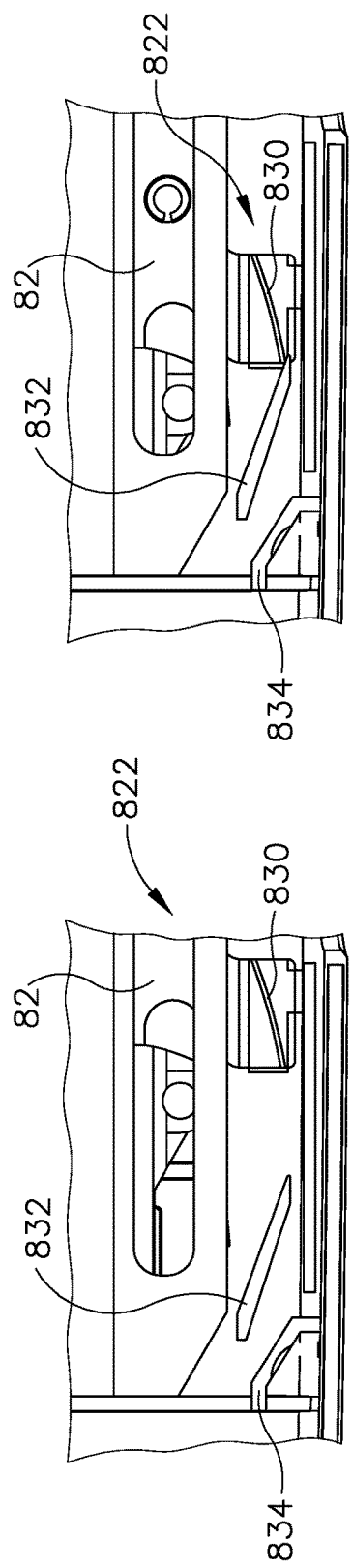

SURGICAL STAPLER WITH END OF STROKE INDICATOR

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAW") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 depicts an exploded rear perspective view of the staple cartridge of FIG. 3;

FIG. 20A depicts an enlarged left side view of the handle assembly of FIG. 14, with the translational feedback generator in an unfired position;

FIG. 20B depicts an enlarged left side view of the handle assembly of FIG. 14, with a firing bar moving from the unfired position toward a fired position;

FIG. 20C depicts an enlarged left side view of the handle assembly of FIG. 14, with the translational feedback generator in a fired position;

FIG. 23 depicts a left side view of a left shroud portion of the handle assembly of FIG. 22;

FIG. 24A depicts an enlarged right side view of the audible feedback generator of the handle assembly of FIG. 22, with various components removed for clarity, and with the audible feedback generator in an unfired position;

FIG. 24B depicts an enlarged right side view of the audible feedback generator of the handle assembly of FIG. 22, with various components removed for clarity, and with the audible feedback generator moving toward the fired position;

Figure 1A:
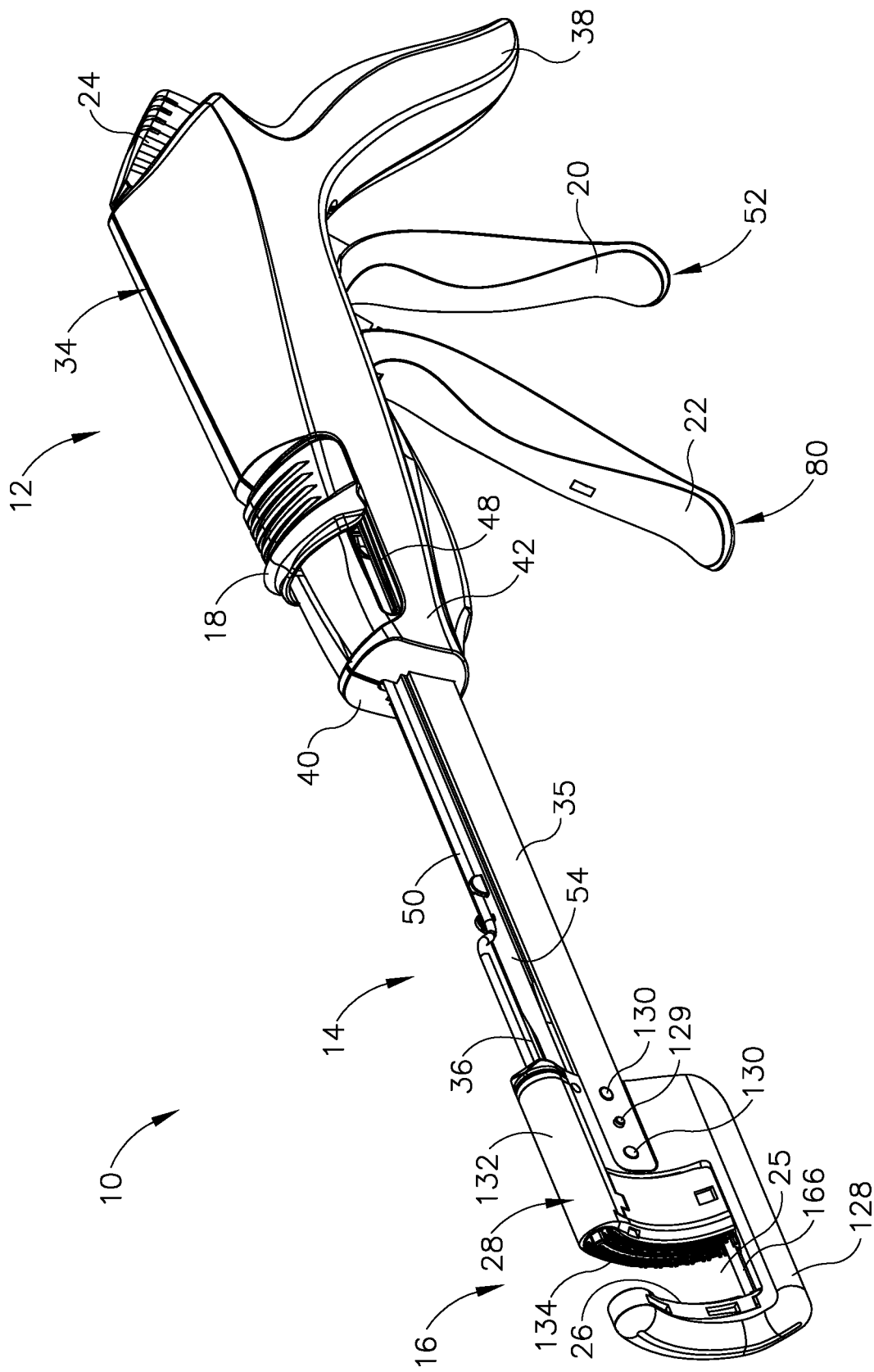
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Exemplary Surgical Stapler

FIG. 1A depicts an exemplary surgical stapling and severing instrument (10) that includes a handle assembly (12), a shaft assembly (14), and an end effector (16) distally projecting from shaft assembly (14). It should be understood that terms such as "proximal," "distal," "right," and "left" are used herein with reference to a clinician gripping handle assembly (12) of surgical stapling instrument (10). Thus, end effector (16) is distal with respect to the relatively proximal handle assembly (14). Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. patent application Ser. No. 14/813,242 entitled "Surgical Instrument Comprising Systems for Assuring the Proper Sequential Operation of the Surgical Instrument," filed on Jul. 30, 2015, issued as U.S. Pat. No. 10,194,193 on Feb. 5, 2019, the disclosure of which is incorporated by reference herein.

Figure 1B:
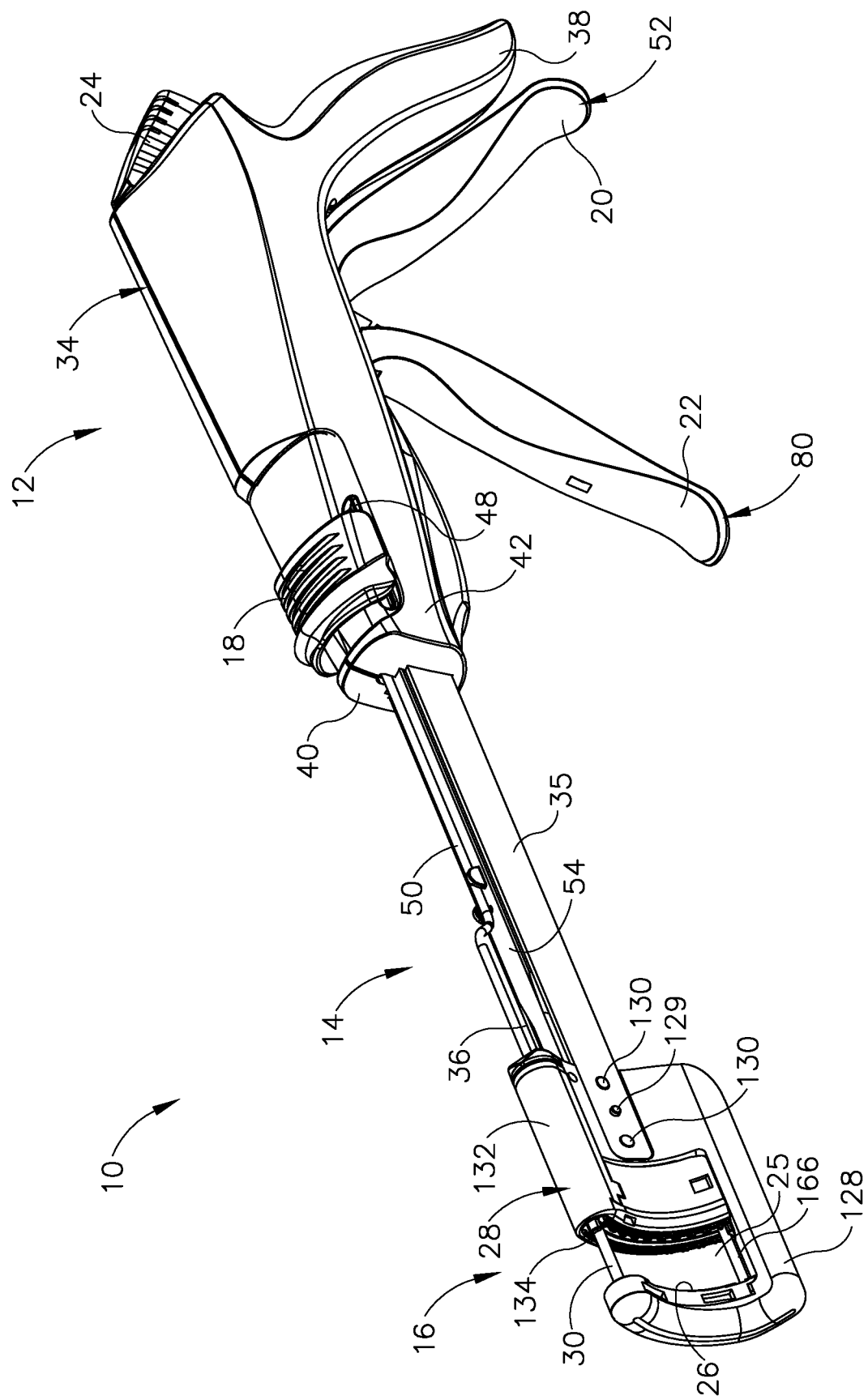
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations such that end effector (16) is configured to receive tissue laterally within a gap (25) between an anvil (26) and a cartridge (28) of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (32) (see FIG. 6) for treatment. Additional details regarding these exemplary actuation mechanisms will be provided below in greater detail.

A. Exemplary Handle Assembly and Shaft Assembly

Figure 2A:
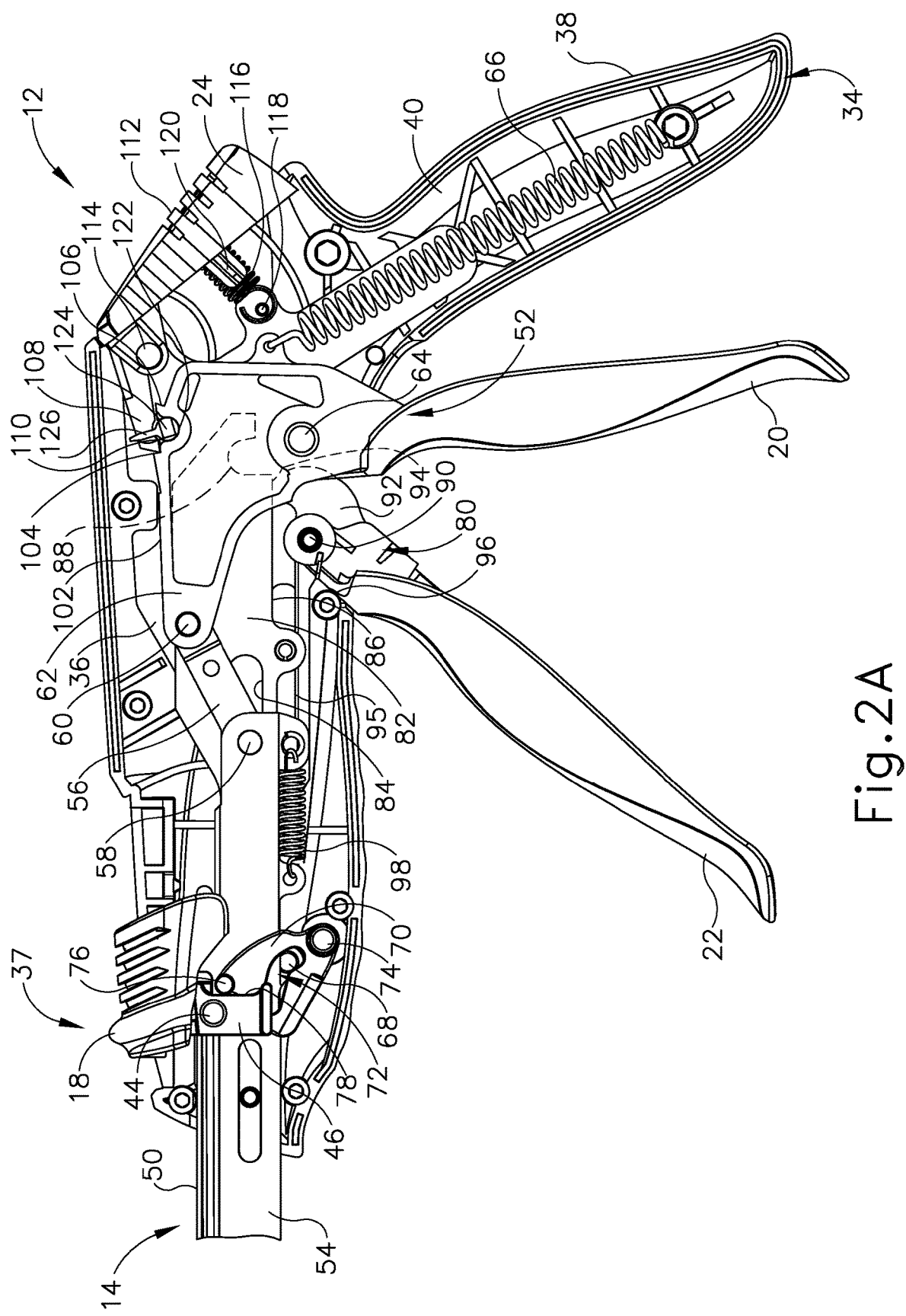
FIG. 2A depicts a right side view of a handle assembly of the surgical stapling instrument of FIG. 1A, with various components removed for clarity, and with the pin actuation mechanism in a closed position and the staple cartridge in the open position.

As shown in FIGS. 1A and 2A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife (32) (see FIG. 6). Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). FIG. 1A shows retaining pin actuation mechanism (37), which includes slide (18), in the open configuration, whereas FIG. 2A shows retaining pin actuation mechanism (37) in the closed configuration in greater detail. With respect to FIG. 2A, slide (18) is mounted on an upper surface of handle housing (34) and is configured to linearly translate between proximal and distal positions. Slide (18) connects to posts (44), which extend laterally outwardly from a push rod driver (46), through slots (48) (see FIG. 1A). Push rod driver (46) is restrained within handle housing (34) along longitudinal movement by slots (48). Push rod driver (46) is connected to a proximal end of a push rod (50). A distal end of push rod (50) connects to retaining pin (30) (see FIG. 6) such that distal movement of slide (18) causes push rod (50) to similarly slide proximally along shaft assembly (14) for moving retaining pin (30) (see FIG. 6) to the closed configuration, which will be discussed below in greater detail.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 3) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Right and left closure links (56) are respectively pivotally attached at the right and left proximal ends of closure member (54) by an integral closure link pin (58). At an opposite end of the closure links (56), closure links (56) are pivotally attached to another integral closure link pin (60). Closure link pin (60) connects closure links (56) to a slotted closure arm link (62), which is pivotally mounted to handle frame plates (35, 36) at a closure trigger pin (64). Closure trigger (20) descends from the slotted closure arm link (62) for pivotal rotation about closure trigger pivot pin (64) both toward and away from hand grip (38). A closure spring (66) housed within hand grip (38) is secured to the slotted closure arm link (62) to provide a desired resistance when the operator squeezes closure trigger (20) toward hand grip (38), and to bias closure trigger (20) toward the open position.

Closure member (54) is further configured for directing movement of tissue retaining pin actuation mechanism (37) to automatically direct movement of the retaining pin (30) to the closed configuration while the operator squeezes closure trigger (20). Such automation may be useful in the event that the operator did not manually move the slide (18) to the distal position before actuating trigger (20). Closure member (54) includes posts (68), which extend laterally on each opposing side of closure member (54) within handle housing (34). Posts (68) slidably connect to a yoke (70) via L-shaped slots (72). Yoke (70) is pivotally mounted within handle housing (34) by a pivot pin (74). Yoke (70) further includes cam pins (76) that are configured to push camming surfaces (78) on push rod driver (46). Thus, actuating closure trigger (20) to an intermediate position shown in FIG. 2A directs the closure member (52) distally and, in turn, causes yoke (70) to engage push rod driver (46) and force retaining pin (30) (see FIG. 1B) to the closed position. Slide (18) is thereby dragged along handle housing (34) from the proximal position to the distal position in the event that the operator did not manually manipulate slide (18) to the distal position before actuating trigger (20).

Figure 1C:
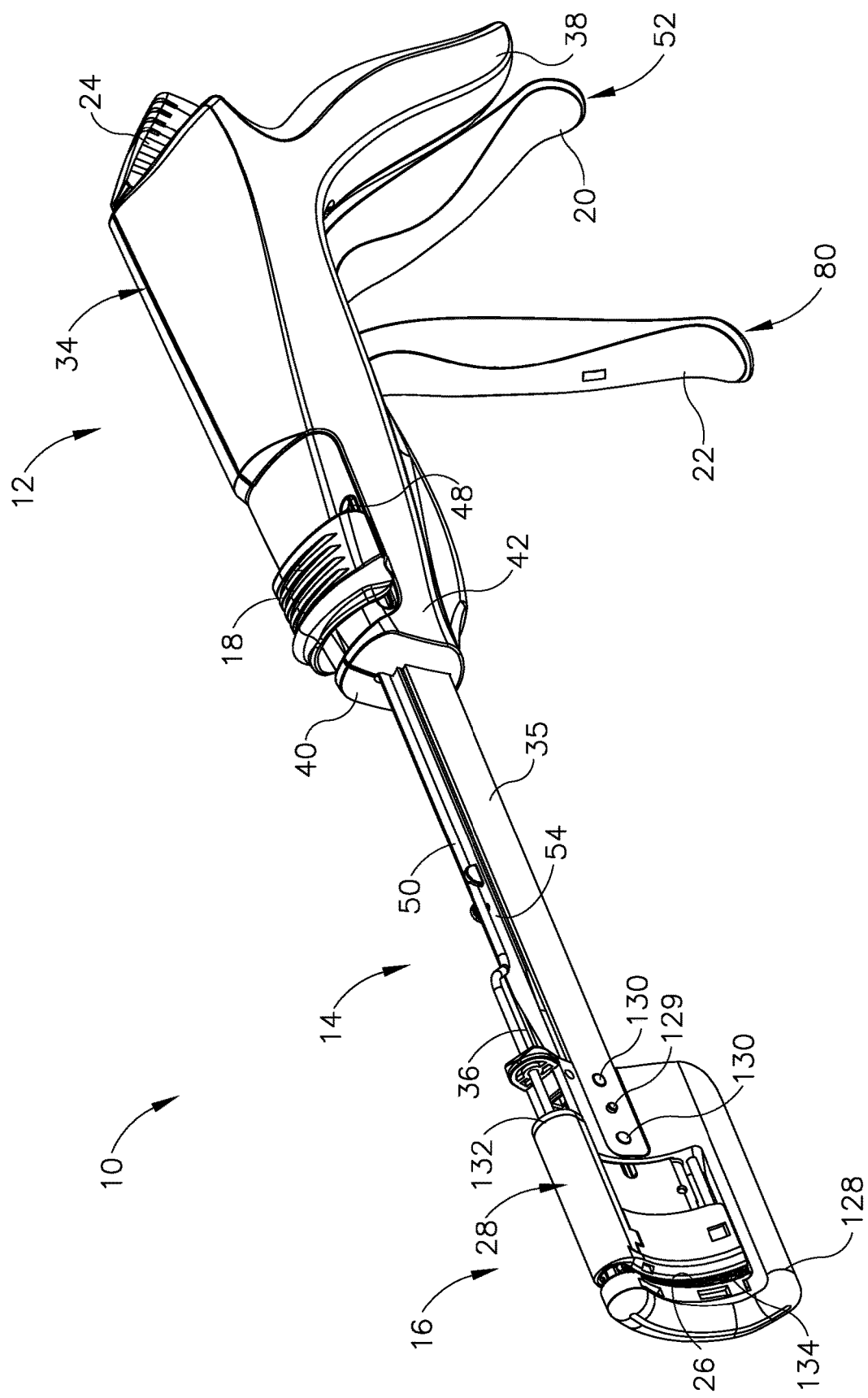
FIG. 1C depicts a right front perspective view of the surgical stapling instrument of FIG. 1A with the pin actuation mechanism in the closed position and the staple cartridge in a closed position via actuation of a closure mechanism.
Figure 1D:
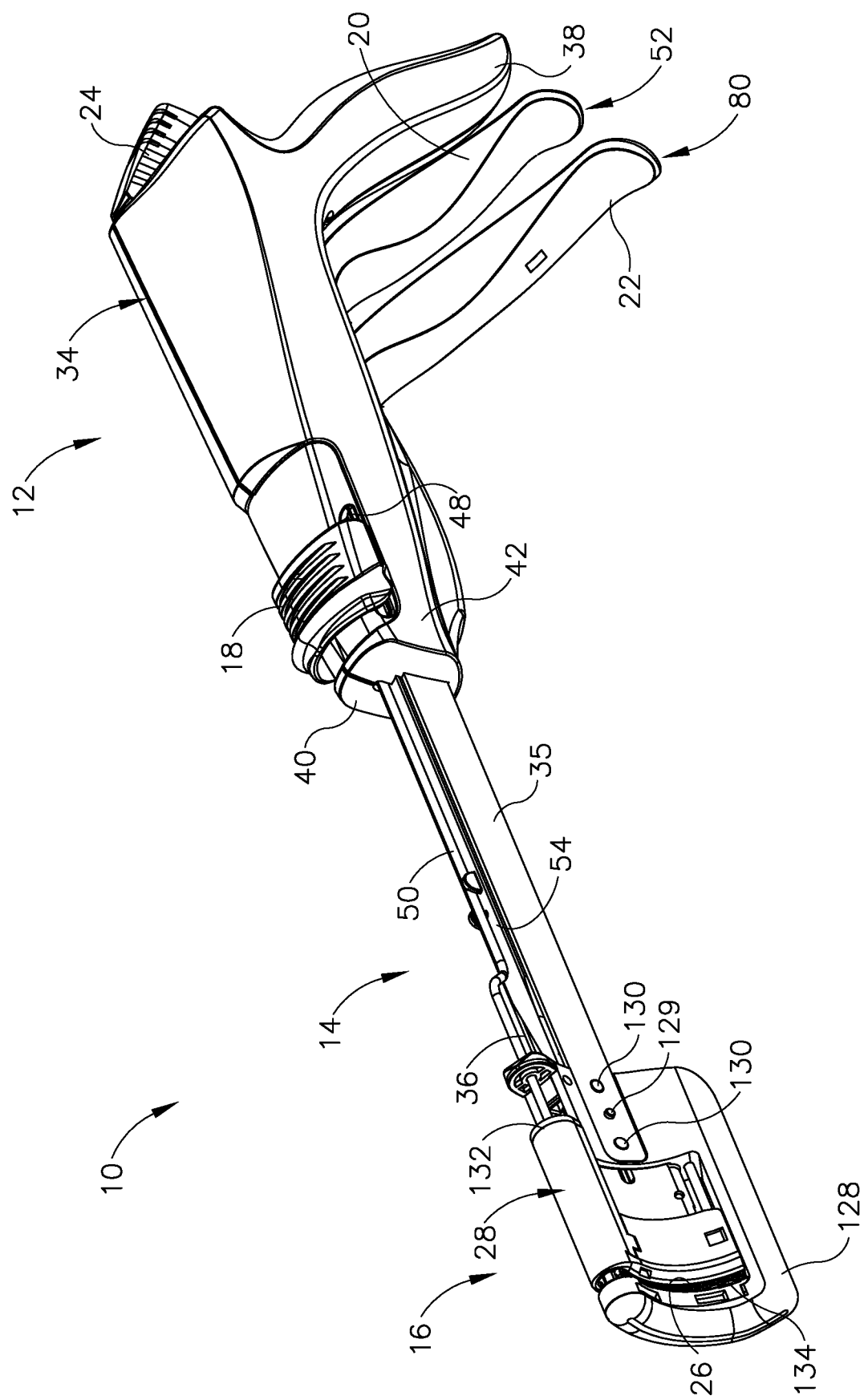
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.
Figure 2B:
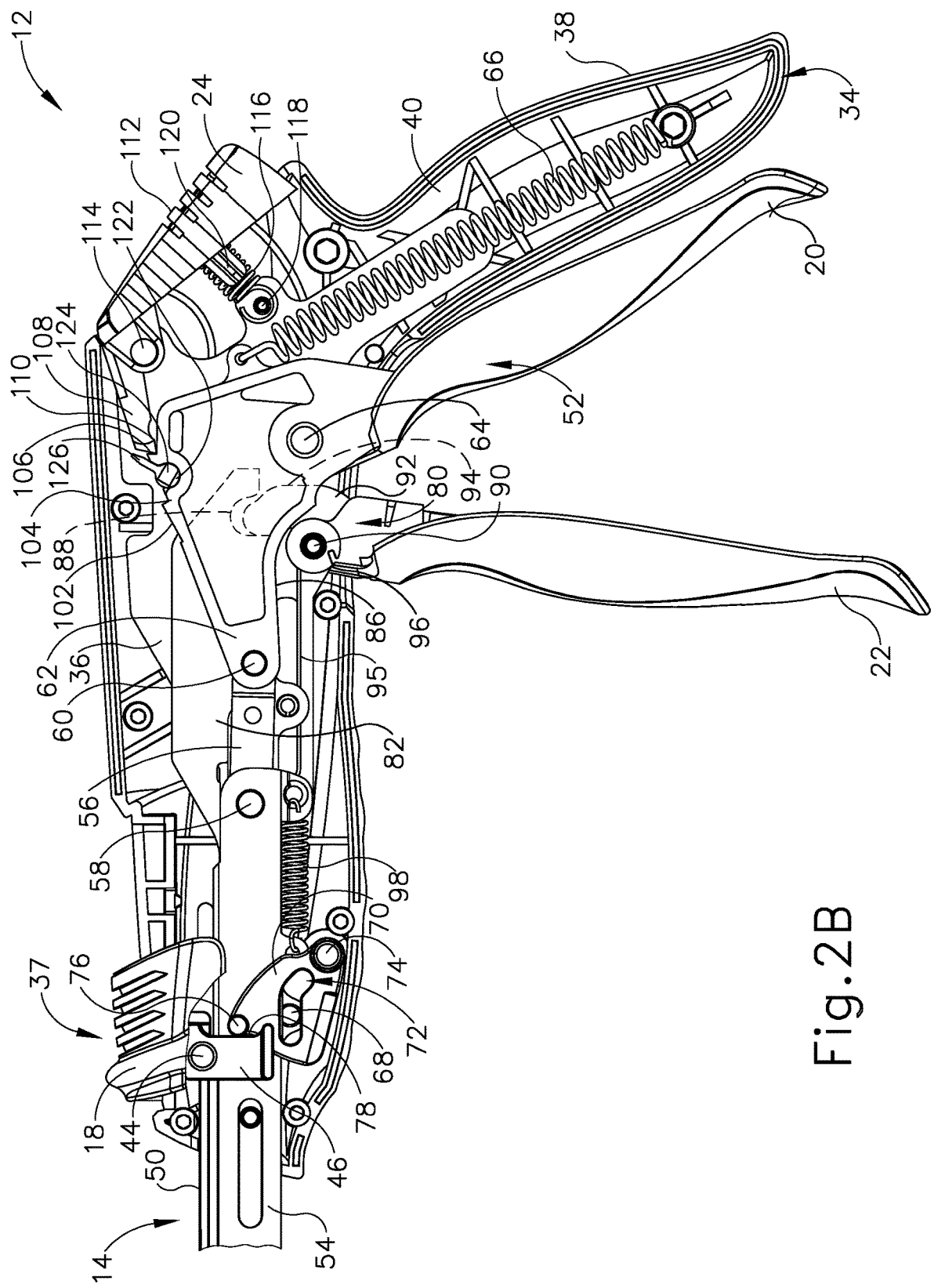
FIG. 2B depicts a right side view of the handle assembly of the surgical stapling instrument of FIG. 1A, with various components removed for clarity, and with the pin actuation mechanism in the closed position and the staple cartridge in the closed position via actuation of the closure mechanism.
Figure 2C:
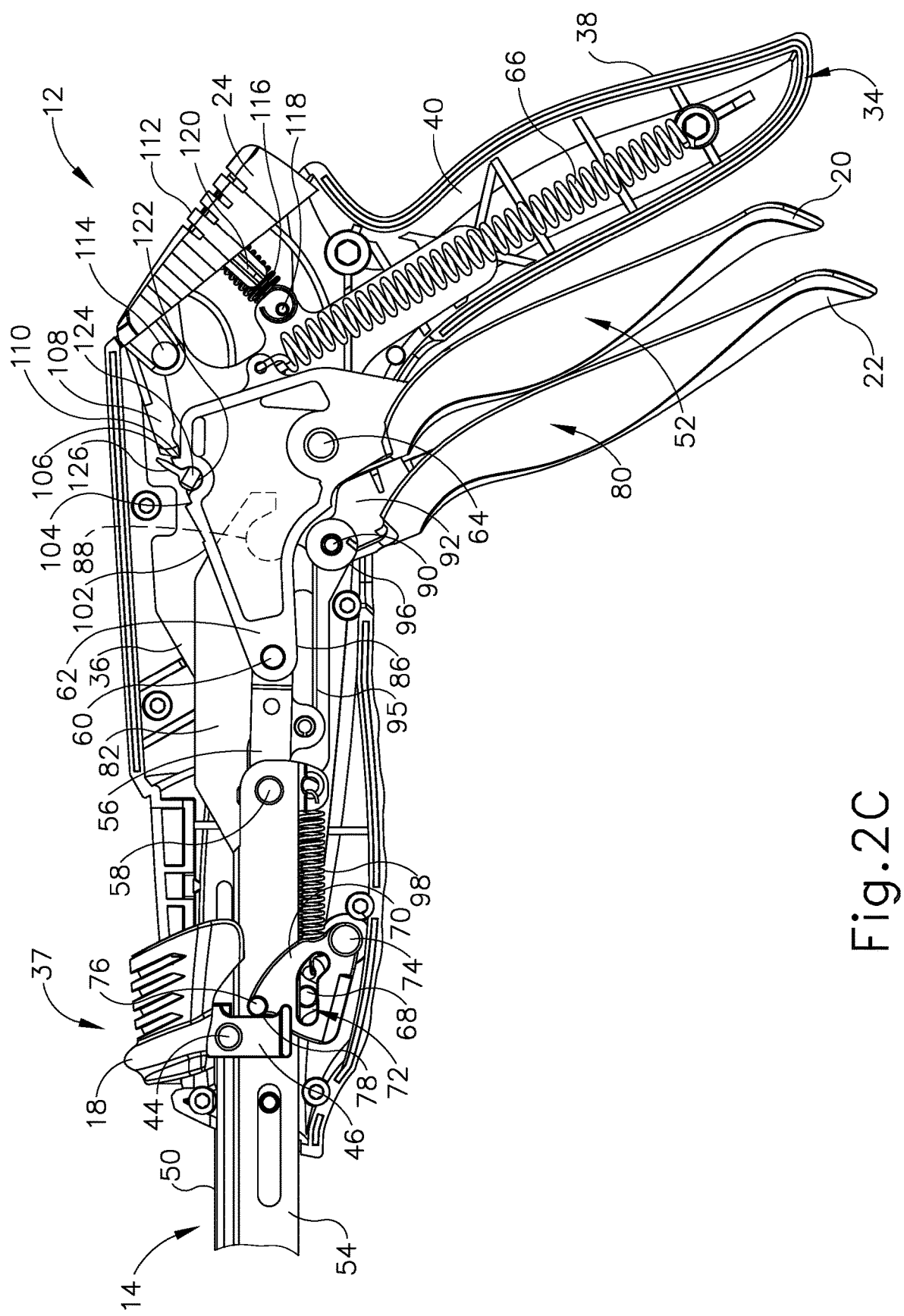
FIG. 2C depicts a right side view of the handle assembly of the surgical stapling instrument of FIG. 1A, with various components removed for clarity, and with the pin actuation mechanism and the staple cartridge in the closed positions and the firing trigger in the fired position for stapling and cutting tissue of a patient.

The operator further squeezes the closure trigger (20) to the hand grip (38) as shown in FIGS. 1C and 2B to effectively set surgical stapling instrument (10) in the closed configuration prior to forming the staples (not shown) and severing the tissue as discussed briefly above. Exemplary handle assembly (12) is configured to form the staples (not shown) and sever the tissue via a firing mechanism (80) upon operator manipulation of firing trigger (22) toward closure trigger (20) as shown in FIGS. 1D and 2C. With respect to FIGS. 1C, 1D, 2B, and 2C, firing mechanism (80), which includes firing trigger (22), has a firing bar (82) extending distally from handle assembly (12) and within end effector (16). A distal end of firing bar (82) cooperates with cartridge (28) as discussed below in greater detail, whereas a proximal end of firing bar (82) is operatively connected to firing trigger (80) for selective firing thereof.

Firing bar (82) has a rectangular receiving slot (84) (see FIG. 2A) in a portion of firing bar (82) positioned within handle housing (34). Integral closure link pin (58) extends through receiving slot (84). The underside of the proximal end portion of firing bar (82) has a sliding surface (86). The proximal end portion of firing bar (82) also has a terminal side engagement surface (82) extending from sliding surface (86). Firing trigger (22) is pivotally mounted to handle frame plates (35, 36) by a firing trigger pin (90) spaced from closure trigger pin (64) such that each of pins (90, 64) pivot about mutually independent axes. Firing trigger (22) includes an arcuate firing trigger link (92) extending from firing trigger (22) at firing trigger pin (90) to an apex (94), which rests on sliding surface (86) of the proximal end portion of firing bar (82). Within handle assembly (12), firing trigger (22) is attached to firing trigger spring arms (95, 96), respectively. Firing trigger spring arms (95, 96) support a torsion spring (not shown) on the right half of firing trigger (22). Finally, a firing bar return spring (98) is secured to the underside of firing bar (82) at the portion of firing bar (82) within handle assembly (12) to bias firing bar (82) toward its unactuated position.

As the operator squeezes closure trigger (20) toward hand grip (38), slotted closure arm link (62) and closure links (56) move distally within receiving slot (84) of firing bar (82). This distal movement causes closure member (54) to correspondingly move distally. Likewise, firing bar (82) concurrently moves distally with closure member (54), because integral closure link pin (58), to which closure links (56) are attached, extends through receiving slot (84) in firing bar (82) (see FIG. 2A). Thereby, firing bar (82) is forced distally to form the staples (not shown) in the tissue and/or sever the tissue with knife (32) (see FIG. 6). Finally, the operator may fully squeeze firing trigger (22) toward hand grip (38) to "fire" surgical stapling instrument (10) and force firing bar (82) further distally to form the staples (not shown) and sever the tissue. This distal movement of firing bar (82) may also be referred to herein as "firing" the firing bar (82) to the actuated or "fired" position.

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release the hand grip (38) to free one or more hands for another task during the surgical procedure and, when desired, release surgical stapling instrument (10) from its locked position by release button (24). By way of example, surgical stapling instrument (10) has an intermediate closure detent position and a closure detent position. With respect to FIGS. 2A-2C, the top side of the slotted closure arm link (62) has a clamp sliding surface (102) that displays an intermediate detent (104) and a closure detent (106). A release pawl (108) slides on clamp sliding surface (102) and may engage intermediate and closure detents (104,106). Release pawl (108) has a laterally extending pawl lug (110) at its distal end.

Release pawl (108) is located within handle assembly (12) and is integrally formed with release button (24), which is situated exterior of handle housing (34) for manipulation by the operator. Release button (24) has a thumb rest (112) pivotally attached to handle housing (34) by a release trunnion (114). Release button (24) is biased outwardly from handle housing (34) and, therefore, release pawl (108) is biased downwardly toward clamp sliding surface (102) by a release spring (116). Release spring (116) is mounted to handle housing (34) by a spring retention pin (118) and is mounted to release button (24) by a button spring post (120). Slotted closure arm link (62) has an arcuate recess (122) located between intermediate and closure detents (104, 106). Resting within arcuate recess (122) for rotational movement are integrally connected left and right hand toggles (124). Each toggle (124) has a toggle arm (126) that is engageable with pawl lug (110).

In order to releasably lock handle assembly (12), toggle arms (126) from pawl lug (110) disengage from pawl lug (110) as closure trigger (20) is squeezed toward hand grip (38). Consequently, as toggle (124) continues to rotate in a clockwise direction, release pawl lug (108) rides up toggle arms (126) and, with continued motion of closure trigger (20), falls into one of intermediate and closure detents (104, 106), depending on the position of closure trigger (20) in use. As release pawl (108) rides up toggle arm (126), release pawl (108) rotates release button (24) clockwise. Release pawl (108) thereby falls into one of intermediate and detents (104, 106) and generates an audible clicking sound alerting the surgeon that one of the intermediate and closure positions have been reached.

In order to release handle assembly (12) from the intermediate or closure positions discussed herein, the surgeon depresses release button (24). In turn, release pawl (108) pivots about release trunnion (114) in a clockwise direction to dislodge pawl lug (110) from one of the intermediate and closure detents (104, 106). As pawl lug (110) is dislodged, pawl lug (110) rides on toggle arms (126) to another position, such as the unactuated position. Therefore, the operator may release closure and firing triggers (20, 22) such that each may return to the unactuated positions FIG. 1A and FIG. 3.

Surgical stapling instrument (10) of the present example includes each of handle frame plates (35, 36), push rod (50), closure member (54), and firing bar (82) extending continuously from handle assembly (12) to end effector (16), thereby defining shaft assembly (14) extending therebetween. Handle frame plates (35, 36), push rod (50), closure member (54), and firing bar (82) of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein, and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Exemplary End Effector

Figure 3:
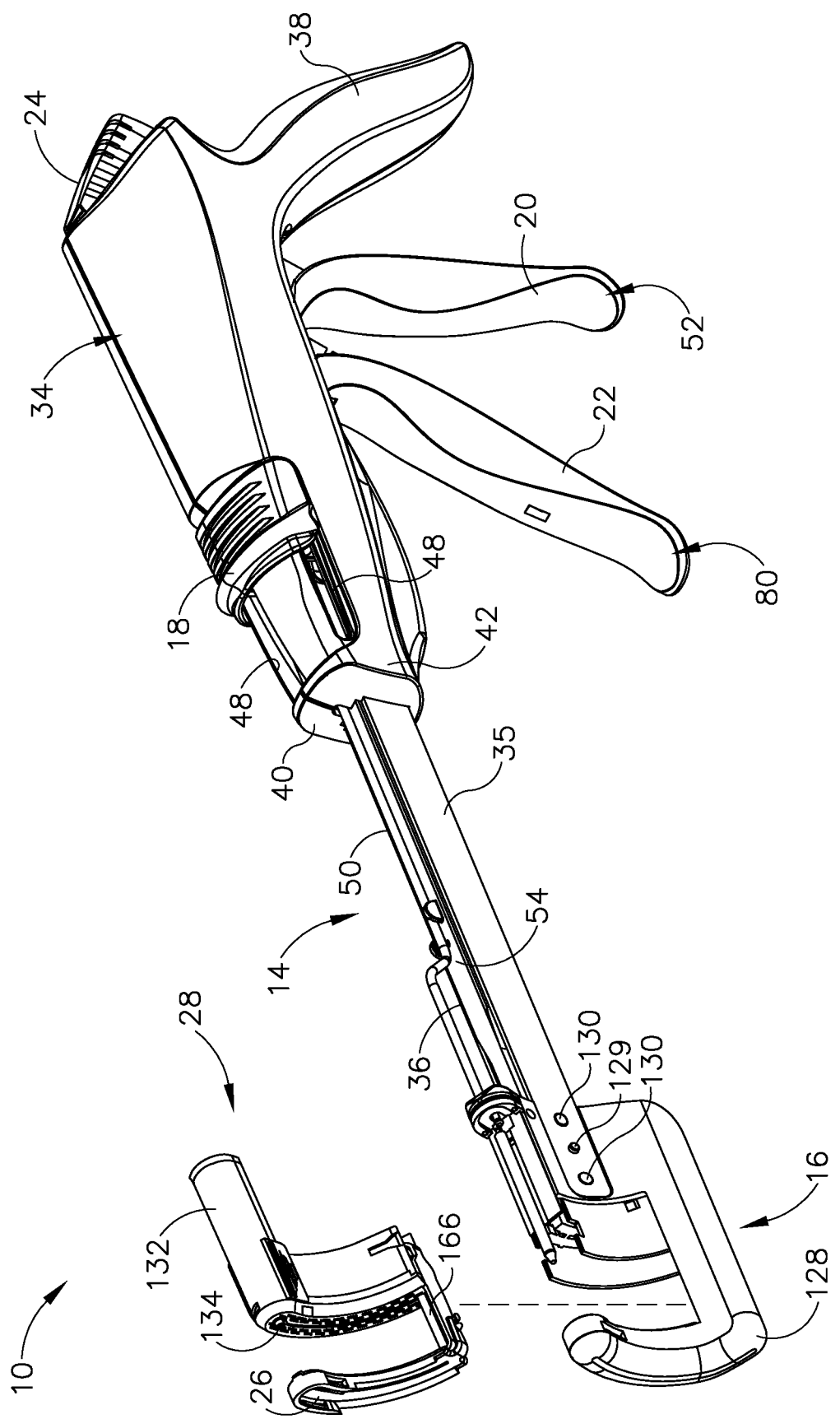
FIG. 3 depicts a partially exploded right front perspective view of the surgical stapling instrument of FIG. 1A showing the staple cartridge removed from a remainder of an end effector.
Figure 4:
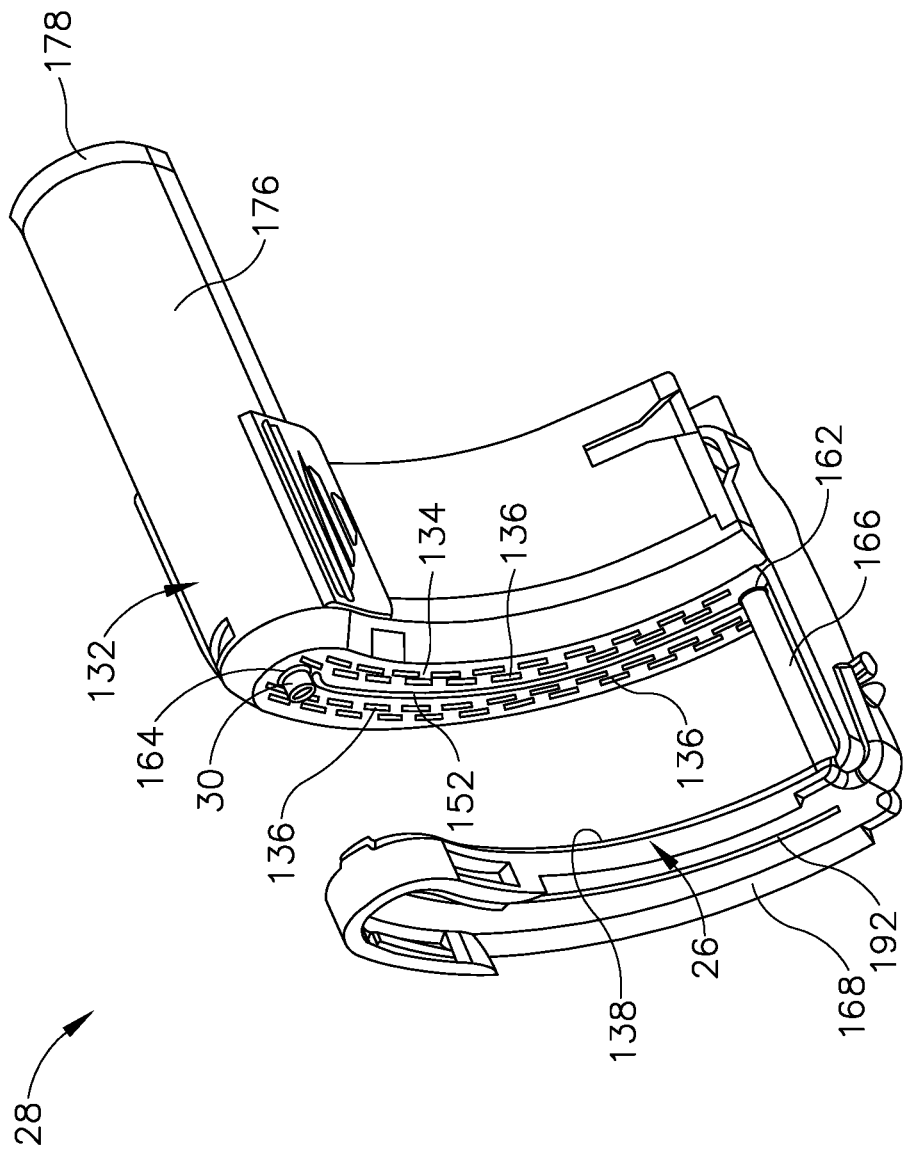
FIG. 4 depicts a right front perspective view of the staple cartridge of FIG. 3.
Figure 5:
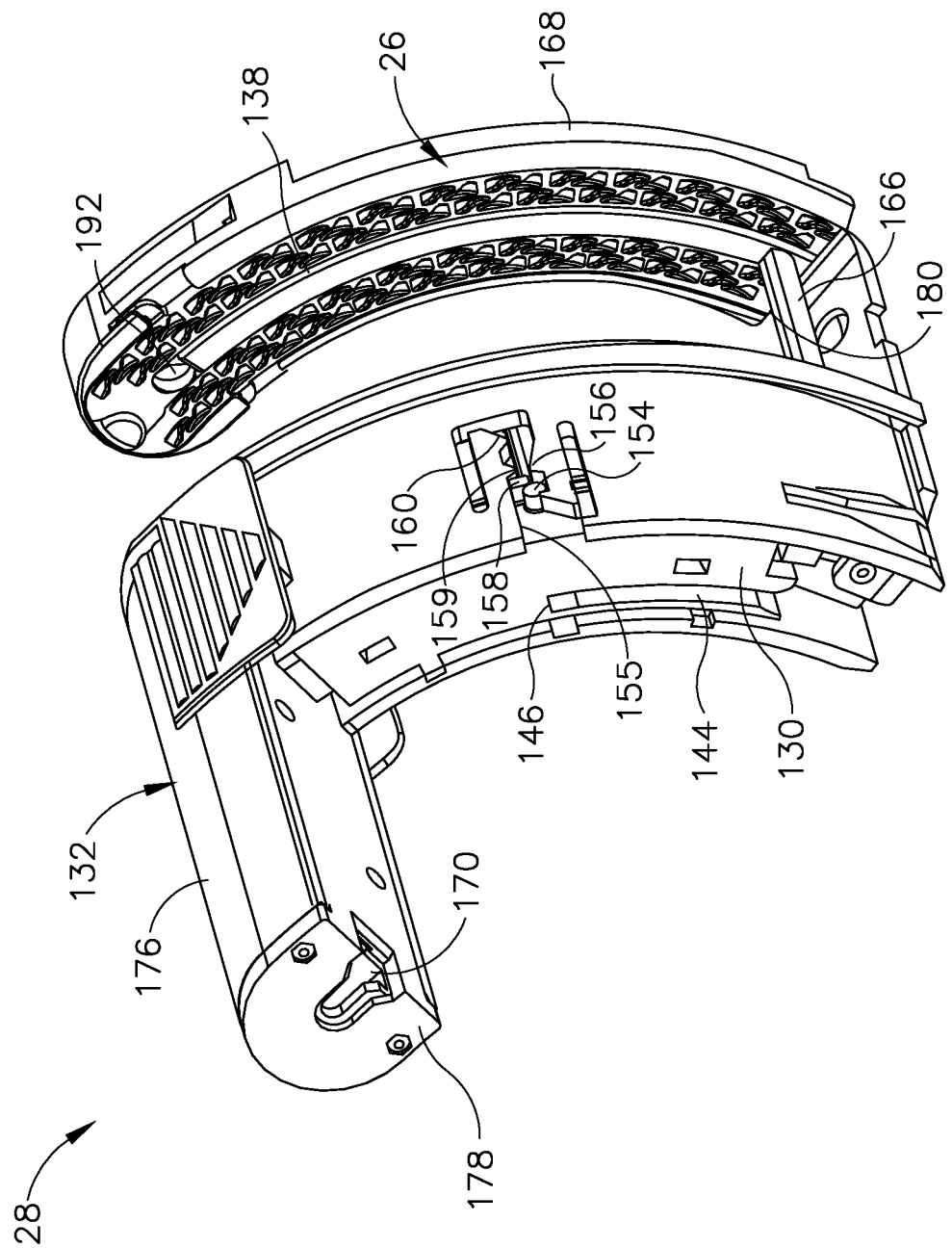
FIG. 5 depicts a rear perspective view of the staple cartridge of FIG. 3.

As also shown in FIGS. 3-5 and discussed briefly above, end effector (16) of the present example includes anvil (26), replaceable cartridge (28) including a plurality of staples (not shown) and knife (32) (see FIG. 6), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End (16) provides a surgical fastening assembly that includes cartridge (28) received within a C-shaped supporting structure (128). The term C-shaped is used throughout the specification to describe the concave nature of supporting structure (128) and cartridge (28). The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure.

Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration. Upon return of cartridge (28) from the closed configuration to the open configuration, cartridge (28) further includes a safety lockout mechanism (131) (see FIG. 7A) configured to inhibit inadvertently re-firing cartridge (28). Safety lockout mechanism (131) will be discussed below in additional detail.

Cartridge (28) includes anvil (26) coupled to a cartridge housing (132). Cartridge (28) also includes retaining pin (30) and a tissue contacting surface (34), which defines a plurality of staple-containing slots (136) in staggered formation in one or more rows on either side of knife (32) (see FIG. 6). Staples (not shown) are fired from cartridge housing (132) against a staple-forming surface (138) of anvil (26) that faces tissue-contacting surface (134) of cartridge housing (132). Cartridge (28) may also include a removable retainer (not shown) for storage between anvil (26) and tissue contacting surface (34) prior to and/or after use in order to inhibit unintended contact with various portions of cartridge (28).

As shown in FIGS. 4-6, cartridge (28) includes a staple driver assembly (140) within cartridge housing (132) and proximally positioned behind the plurality of staples (not shown) within staple-containing slots (136). Driver assembly (140) of the present example is formed as a unitary structure of a plurality of staple drivers (141). Thus, the term "assembly" is not intended to be limited an assembly of individual components, but may also include integrally formed components with unitary structures. Driver assembly (140) is configured to push the staples (not shown) respectively out of staple containing slots (136) and toward anvil (26) for formation. A knife holder (142) is disposed immediately proximal of driver assembly (140) in cartridge housing (132) and defines a slot (144) and ledge (146) for interaction with a knife retractor hook (148) (see FIG. 10B), which is discussed below in greater detail. Knife holder (142) is attached to knife (32) such that knife (32) extends distally from knife holder (142) through a slot (150) in driver assembly (140) and through another slot (152) in cartridge housing (132). Although knife (32) is disclosed as being within cartridge housing (132) in the present example, other configurations may also be used. For example, it will be appreciated that cartridge (28) may alternatively not include knife (32) for alternative treatments.

Knife holder (142) has a detent post (154) that extends through a slot (155) in cartridge housing (132). Detent post (154) is positioned in order to contact a detent protrusion (156) of cartridge slot (155) during the longitudinal travel of knife (132) and knife holder (142). Similarly, driver assembly (140) has a detent post (158) positioned in order to contact proximal and distal detent protrusions (159, 160) of cartridge slot (155).

Knife (32) and slots (150, 152) are positioned such that there is at least one row of staples (not shown) on either side of knife (132). In some versions, two rows of staple slots (136) containing respective rows of staples (not shown) are provided on each side of slot (152) of cartridge housing (132).

Cartridge housing (132) defines two longitudinally extending, generally circular holes (162, 164) at respective ends of knife slot (152). More particularly, hole (162) at a lower portion of cartridge housing (132) is shaped and dimensioned to receive a guide pin (166) through cartridge housing (132). Hole (164) at an upper portion of cartridge housing (132) is shaped and dimensioned to slidably receive retaining pin (30) through cartridge housing (132). Staple slots (136) of the present example are arranged such that the staples (not shown) laterally extend past the generally circular holes (162, 164).

Anvil (26) of the present example includes a plastic cutting washer (168) and a metallic staple-forming surface (138). Anvil (26) is disposed to maintain staple-forming surface (138) in alignment with the staples (not shown) to receive and form the staples (not shown) thereon. Retaining pin (30) is connected to a couplet (170) by a circumferential slot (172) in retaining pin (30) and a groove (not shown) in couplet (170). Couplet (170) is disposed within an arm (176) of cartridge housing (132) and is secured to arm (176) by an end cap (178).

Guide pin (166) and retaining pin (30) include respective slots (180, 182) (see also FIGS. 8-9) into which lower and upper ends (184, 186) of knife (32) are slidably disposed. A proximal end (188) of guide pin (166) is connected to anvil (26), whereas a distal end (190) of guide pin (166) extends from cartridge housing (132) and extends through a slot (192) in anvil (26). Cutting washer (168) slips onto anvil (26) via groove (194). Thereby, cutting washer (168) is configured to trap guide pin (166) in the opening formed by slot (192) in anvil (26) and a cutting surface (157) of anvil (26) for connecting anvil (26) to cartridge housing (132).

Figure 7A:
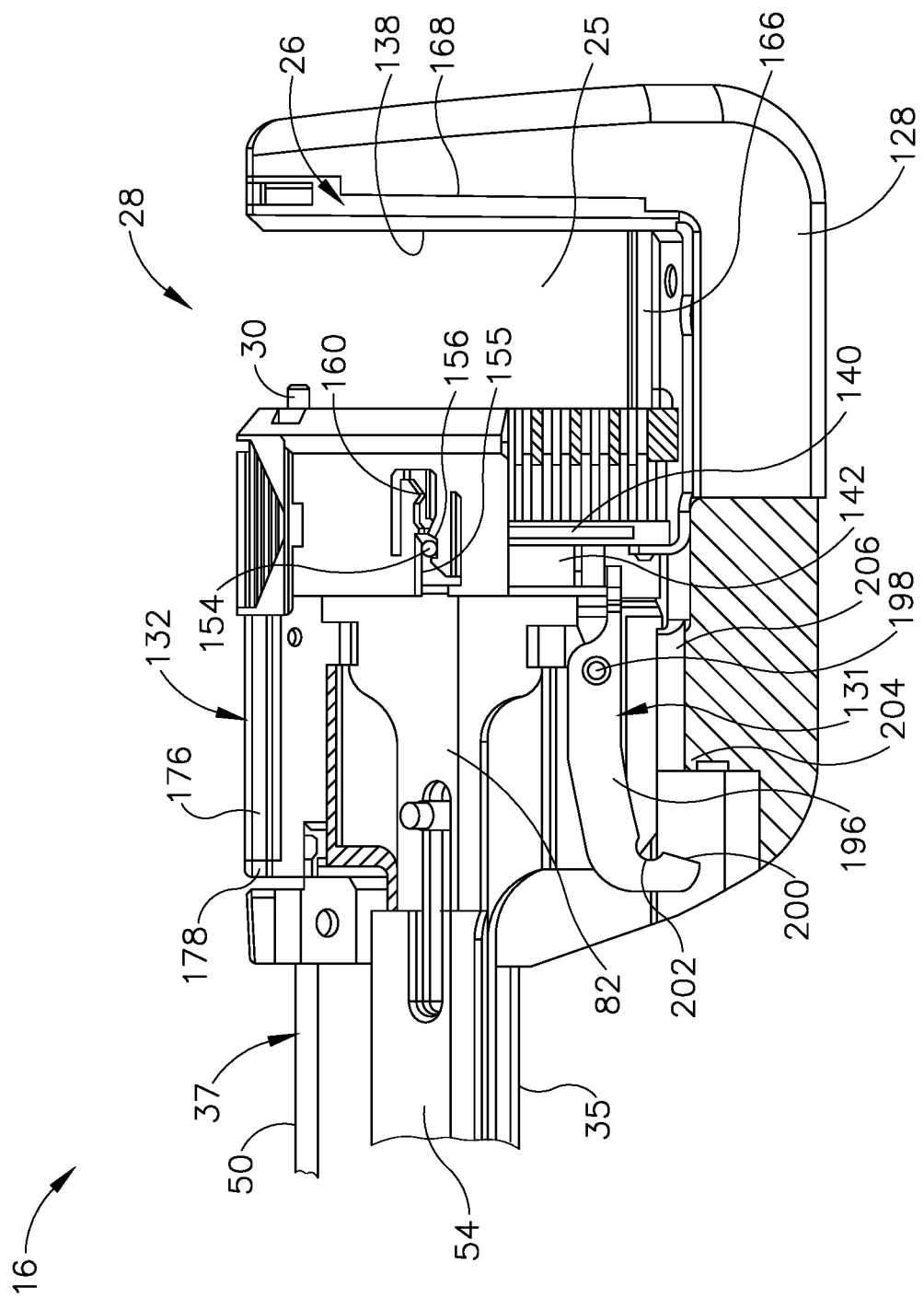
FIG. 7A depicts a left side view of the end effector of FIG. 1A with various components removed for clarity.

Lockout mechanism (131) is shown in FIG. 7A in greater detail. Lockout mechanism (131) is configured to inhibit full proximal movement of cartridge housing (132) to its unactuated position after firing. To this end, lockout mechanism (131) of the present example includes a lockout lever (196) that is pivotally mounted to the distal end of closure member (54) by a pin (198). Lockout lever (196) is spring biased toward the proximal end portion of supporting structure (128) by a spring (not shown). A proximal end portion of lockout lever (196) has a cam surface (200) and a locking groove (202). Supporting structure (128) of end effector (16) also has a ledge (204) that is configured to cooperate with locking groove (202) when lockout mechanism (131) is engaged. In contrast, supporting structure (128) has a base surface (206) configured to cooperate with cam surface (200) when lockout lever (131) is not engaged.

C. Exemplary Actuation of Cartridge

In the present example, cartridge (28) is driven toward anvil (26) via closure member (54) until reaching the closed configuration with tissue positioned between cartridge (28) and anvil (26) as discussed above with respect to handle assembly (12). From the closed configuration, knife (32) and staple driver assembly (140) are further moved toward anvil (26) via firing bar (82) to form staples (not shown) in the tissue, fluidly seal the tissue, and sever the tissue for treating the patient. While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. For example, actuation of firing bar (82) causes driver assembly (140) and knife (32) to move distally toward anvil (26) in the present example. Alternatively, surgical stapling instrument (10) may be reconfigured to selectively fire one of staples (not shown) or knife (32), or selectively fire staples (not shown) and then knife (32), or vice versa. It should therefore be understood that the invention is not intended to be limited to the particular operation of surgical stapling instrument (10) or the associated treatment.

Figure 7B:
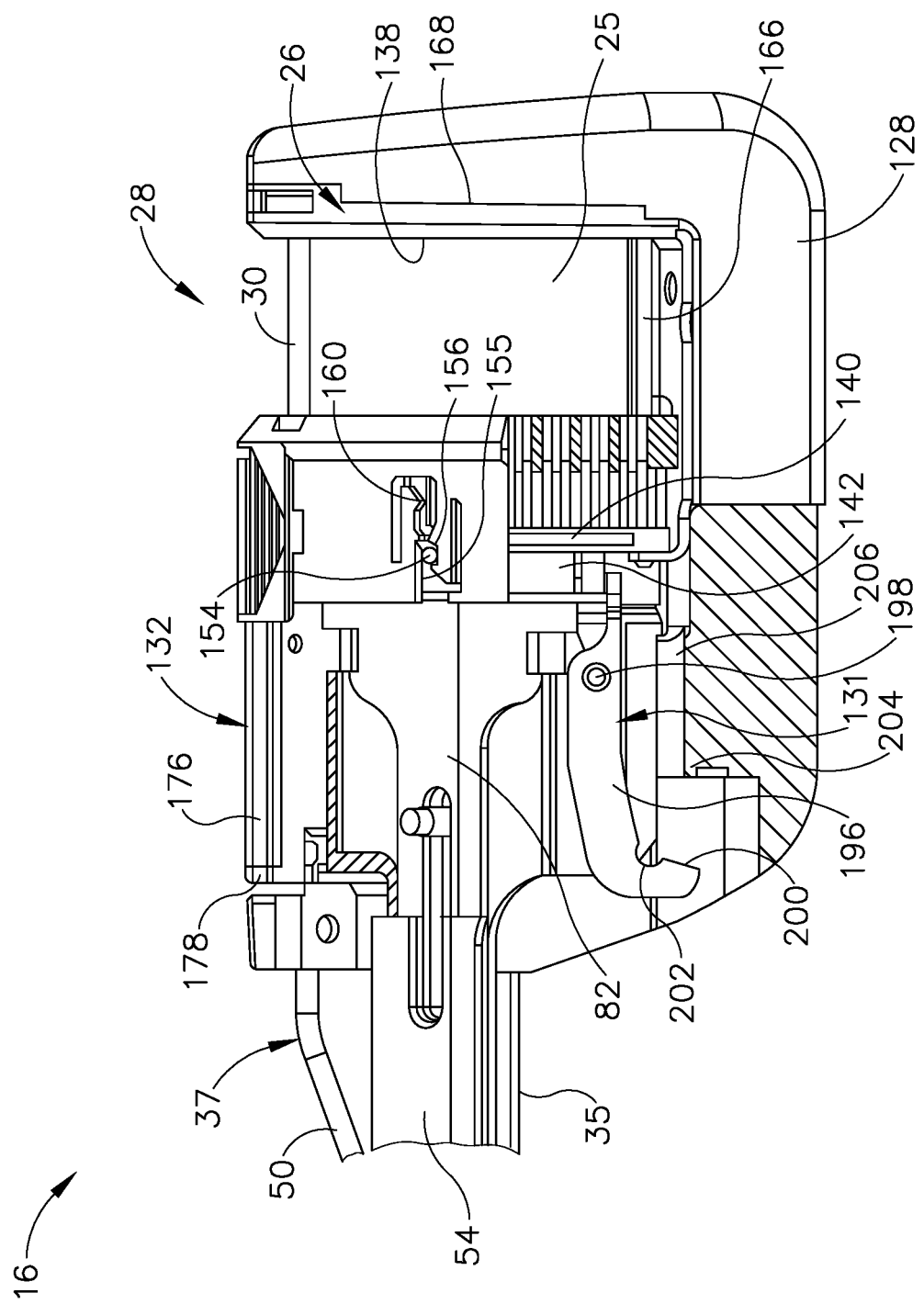
FIG. 7B depicts a left side view of the end effector of FIG. 1A with various components removed for clarity, and with the pin actuation mechanism in a closed position and the staple cartridge in the open position.

As shown in FIG. 7A, cartridge (28) is spaced proximally from anvil (26) to receive tissue within gap (25) in the open configuration. With tissue received between cartridge (28) and anvil (26), the operator manually directs push rod (50) distally via slide (18) as discussed above and shown in FIG. 7B. Push rod (50) is operatively connected to couplet (70) (see FIG. 6), which is connected to retaining pin (30). Thus, distally translating push rod (50) similarly translates retaining pin (30) to extend from cartridge (28) to anvil (26) and capture tissue between retaining pin (30) and guide pin (166).

Figure 7C:
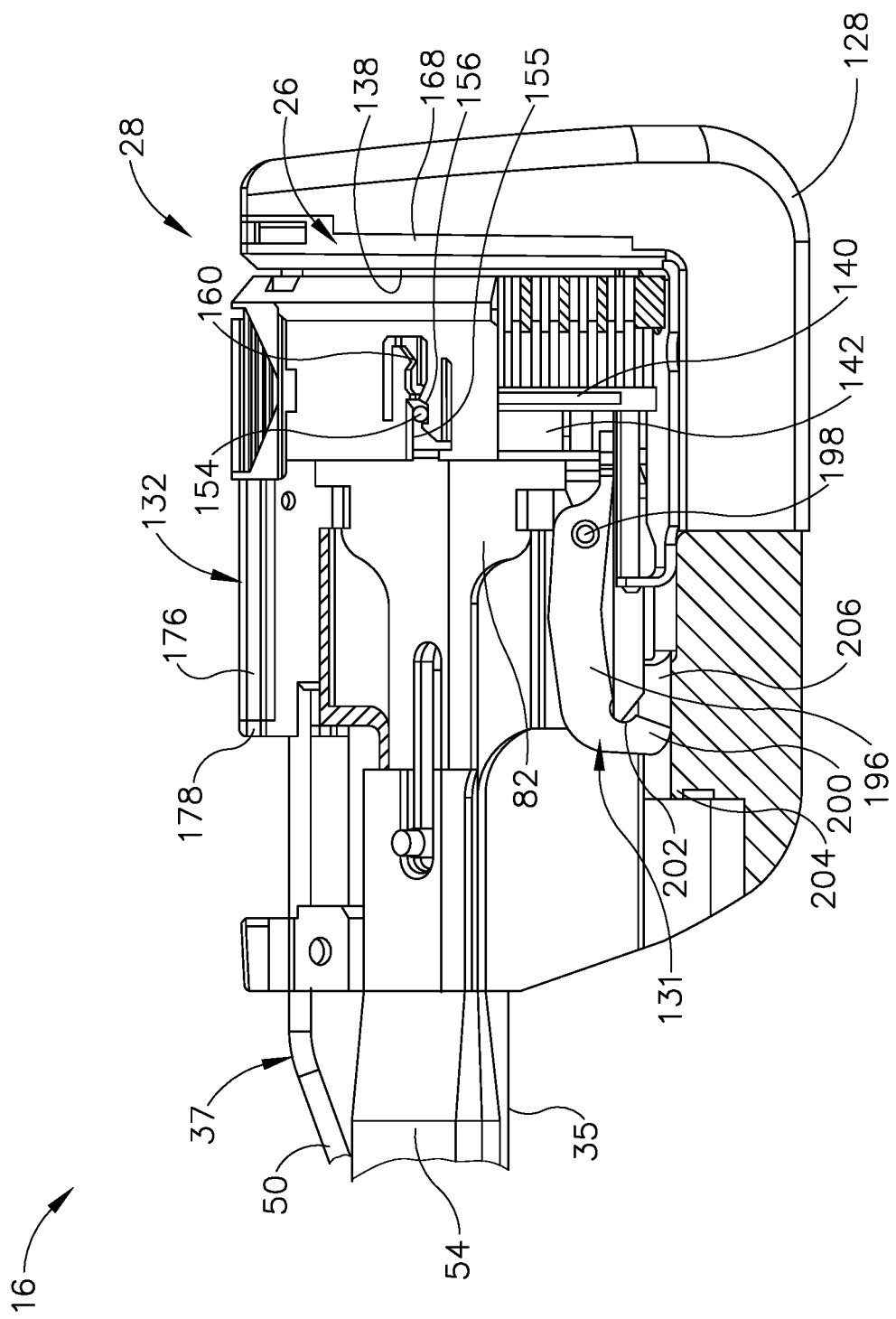
FIG. 7C depicts a left side view of the end effector of FIG. 1A with various components removed for clarity, and with the pin actuation mechanism in the closed position and the staple cartridge in the closed position via actuation of the closure mechanism.
Figure 7D:
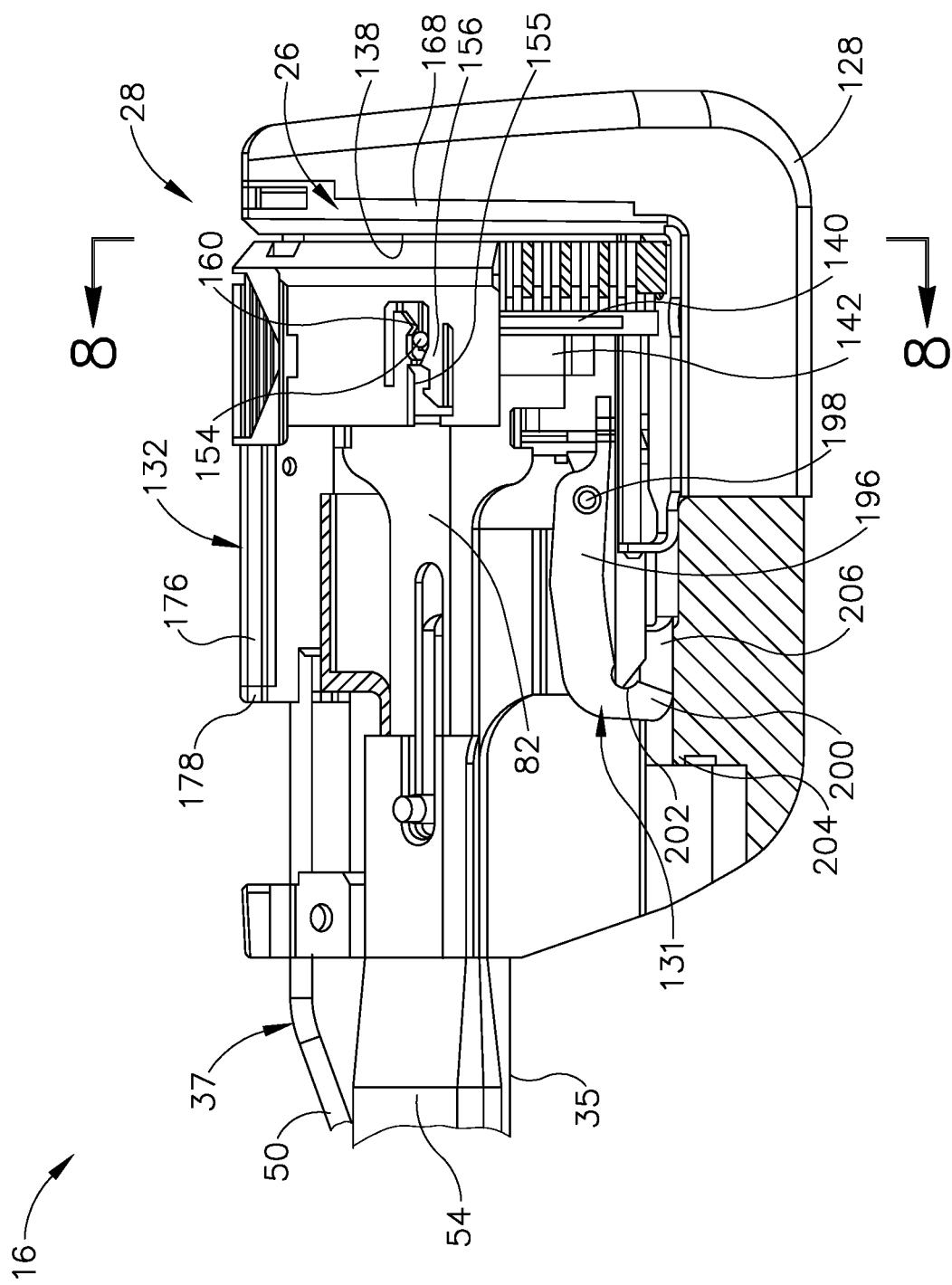
FIG. 7D depicts a left side view of the end effector of FIG. 1A with various components removed for clarity, and with the pin actuation mechanism and the staple cartridge in the closed positions and the firing trigger in the fired position for stapling and cutting tissue of a patient.
Figure 8:
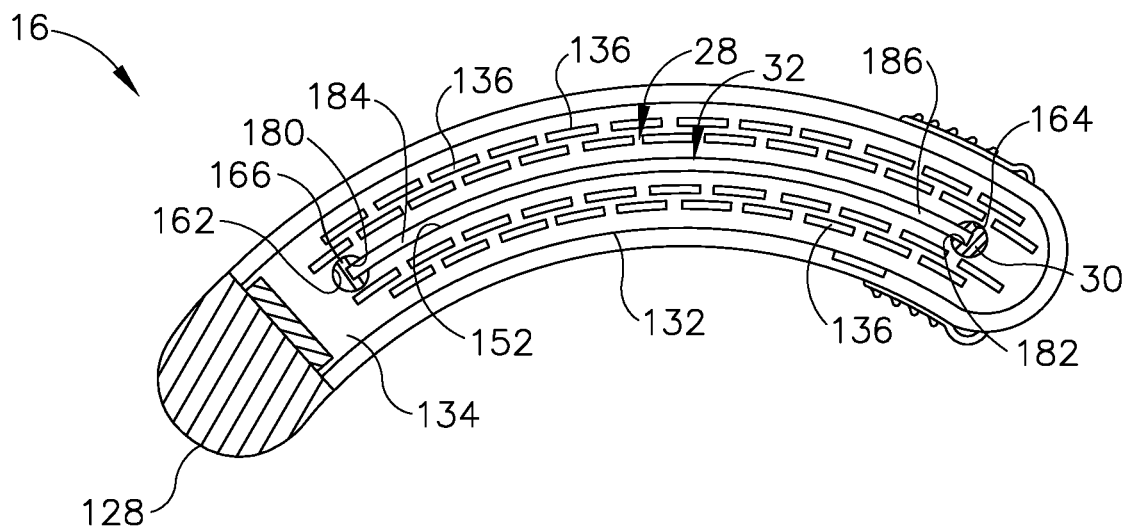
FIG. 8 depicts a cross-sectional view of the end effector of FIG. 7D, taken along section line 8-8 of FIG. 7D.
Figure 9:
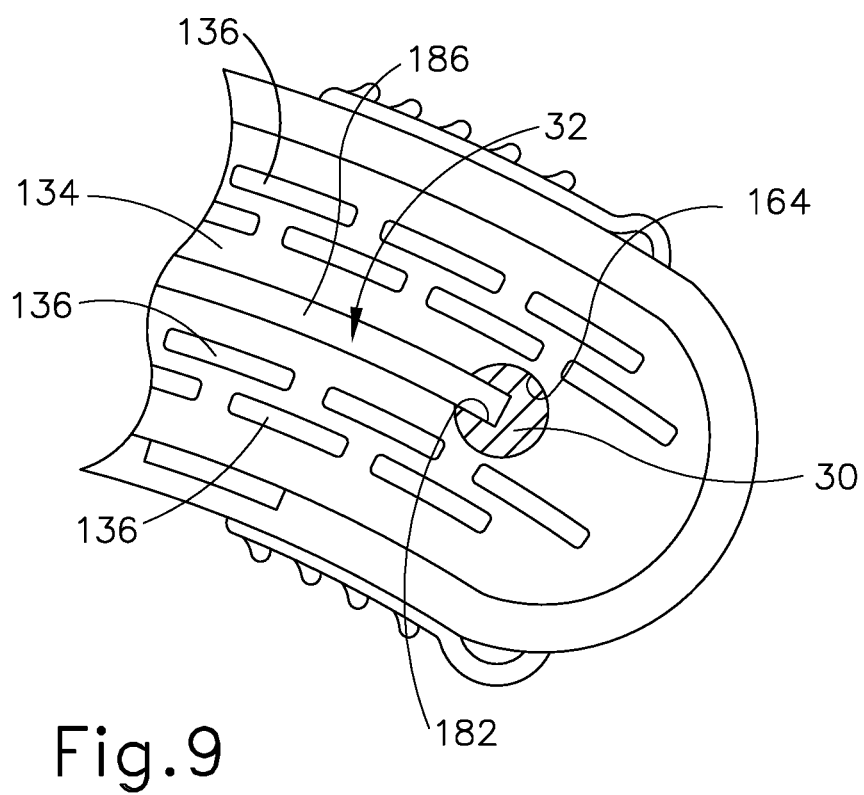
FIG. 9 depicts an enlarged cross-sectional view of a portion of the end effector of FIG. 8.

As shown in FIG. 7C, manipulation of closure trigger (20) (see FIG. 1C) forces closure member (54) to translate distally relative to supporting structure (128) of end effector (16). Closure member (54) supports cartridge (28) thereon such that distal translation of closure member (54) similarly moves firing bar (82) and cartridge (28) toward anvil (26). With cartridge (28) in the closed configuration and the tissue effectively captured in the end effector (16), the operator manipulates firing trigger (22) (see FIG. 1D) toward anvil (26) to the fired position. Distal translation of firing bar (82) causes firing bar (82) to engage knife holder (142), which supports both driver assembly (140) and knife (32) extending through driver assembly (140) as shown in FIG. 7D. In turn, driver assembly (140) directs staples (not shown) from staple slots (136) and against staple-forming surface (138) to form the staples (not shown) within the tissue for fluidly sealing the tissue. As the staples (not shown) are formed, knife (32) continues to translate distally through tissue and into anvil (26) to sever the fluidly sealed tissue. FIGS. 8-9 illustrate the fired cartridge (28) in greater detail, with knife (32) guided along cartridge housing slot (152), guide pin slot (180); and with retaining pin slot (182) between rows of staple slots (136) toward anvil (26).

Figure 10A:
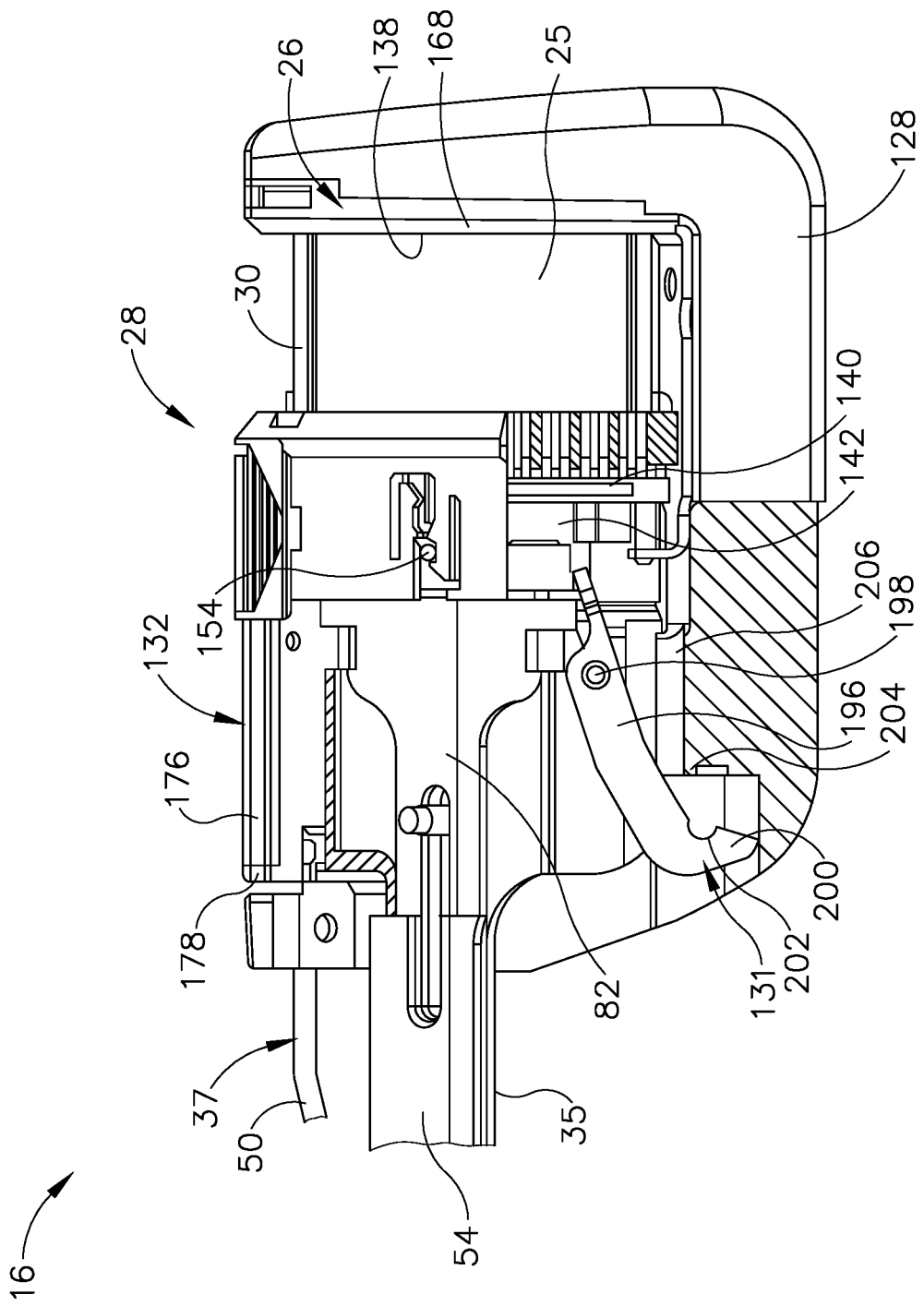
FIG. 10A depicts a left side view of the end effector of FIG. 1A, with various components removed for clarity, with the staple cartridge returned to the open position after actuating the firing trigger.
Figure 10B:
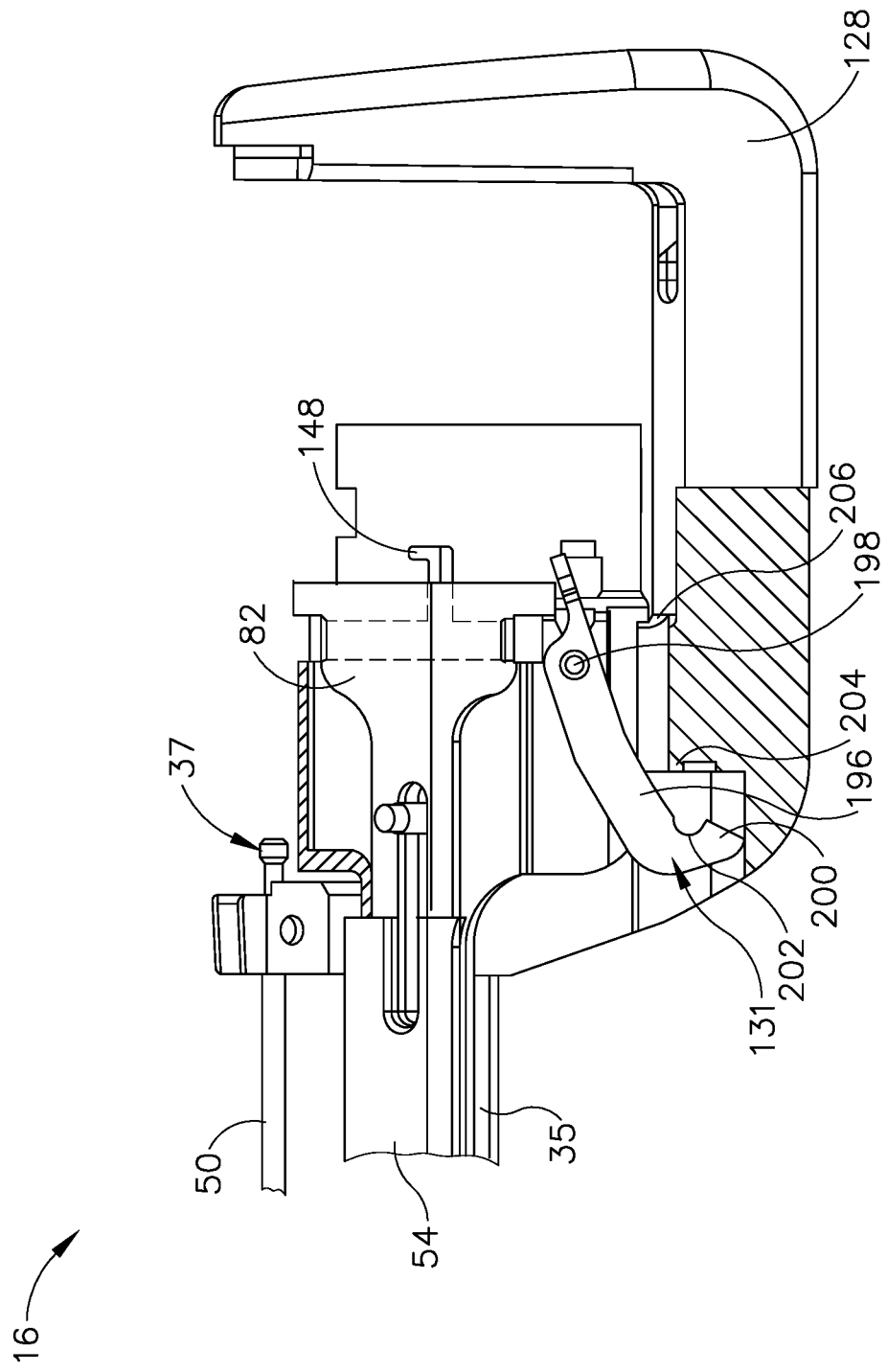
FIG. 10B depicts a left side view of the end effector of FIG. 1A, with various components removed for clarity, with the staple cartridge removed from the remainder of the end effector.
Figure 11:
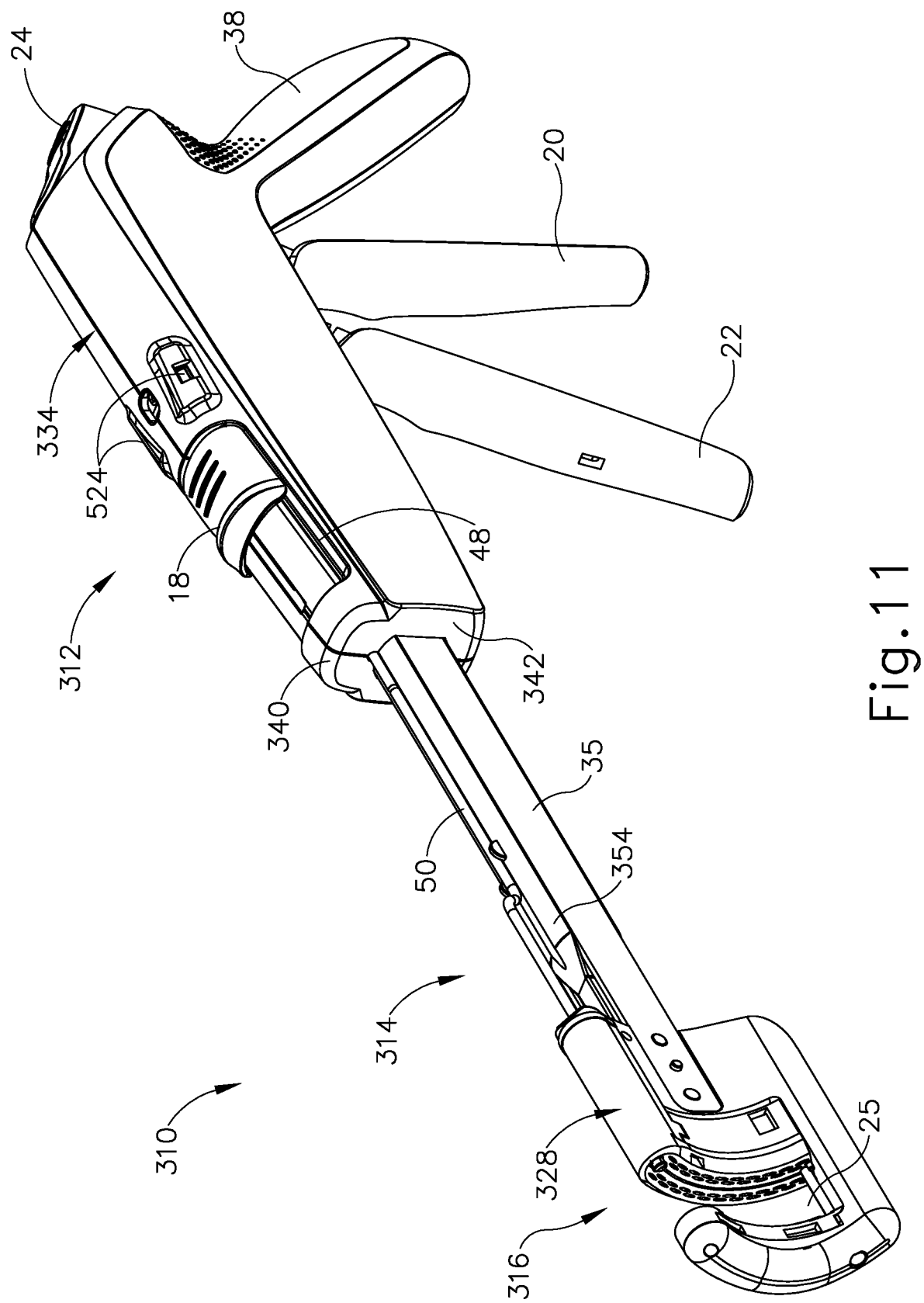
FIG. 11 depicts a right perspective view of another exemplary surgical stapling instrument.
Figure 12:
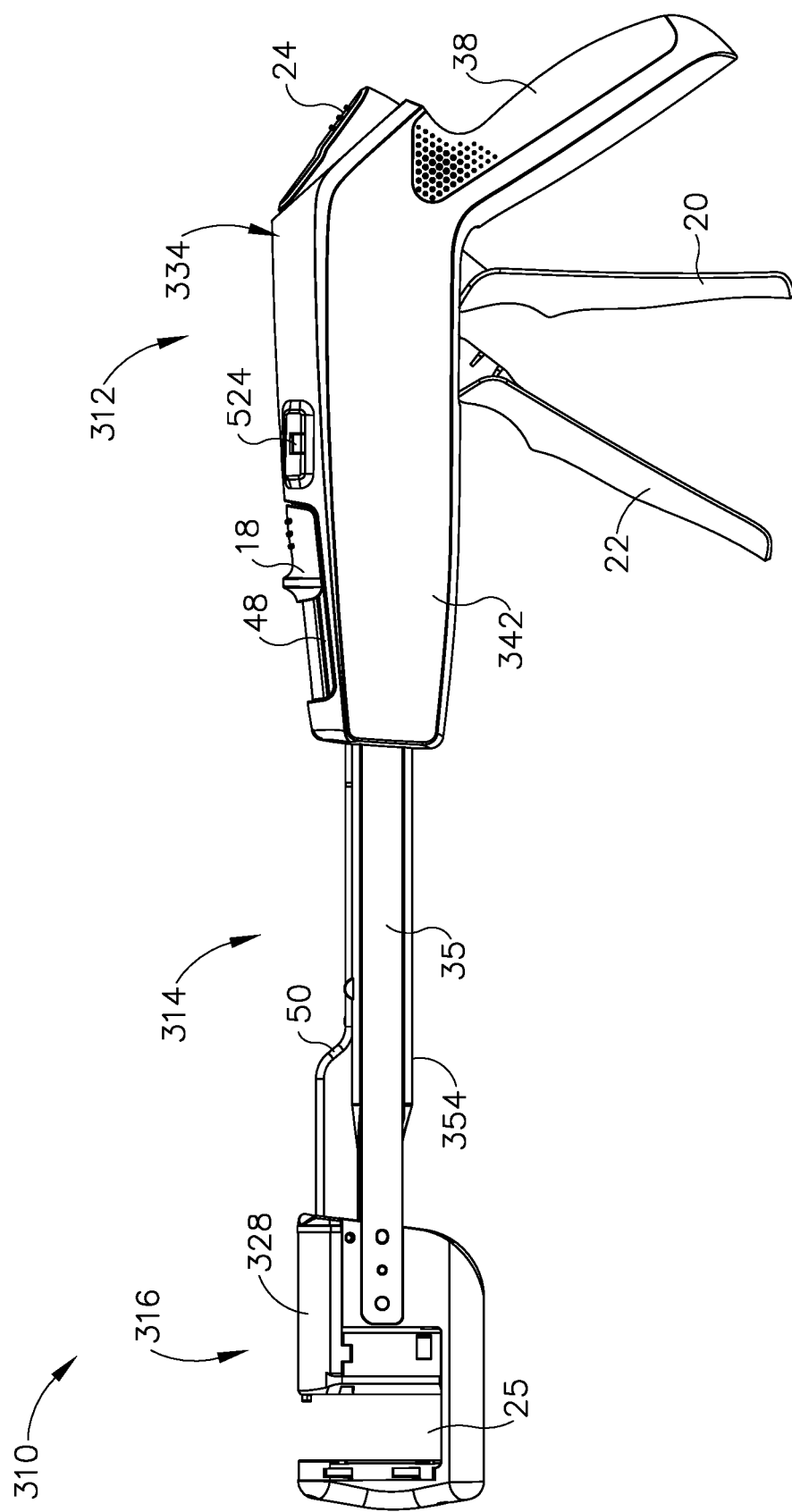
FIG. 12 depicts a right side view of the surgical stapling instrument of FIG. 11.
Figure 13:
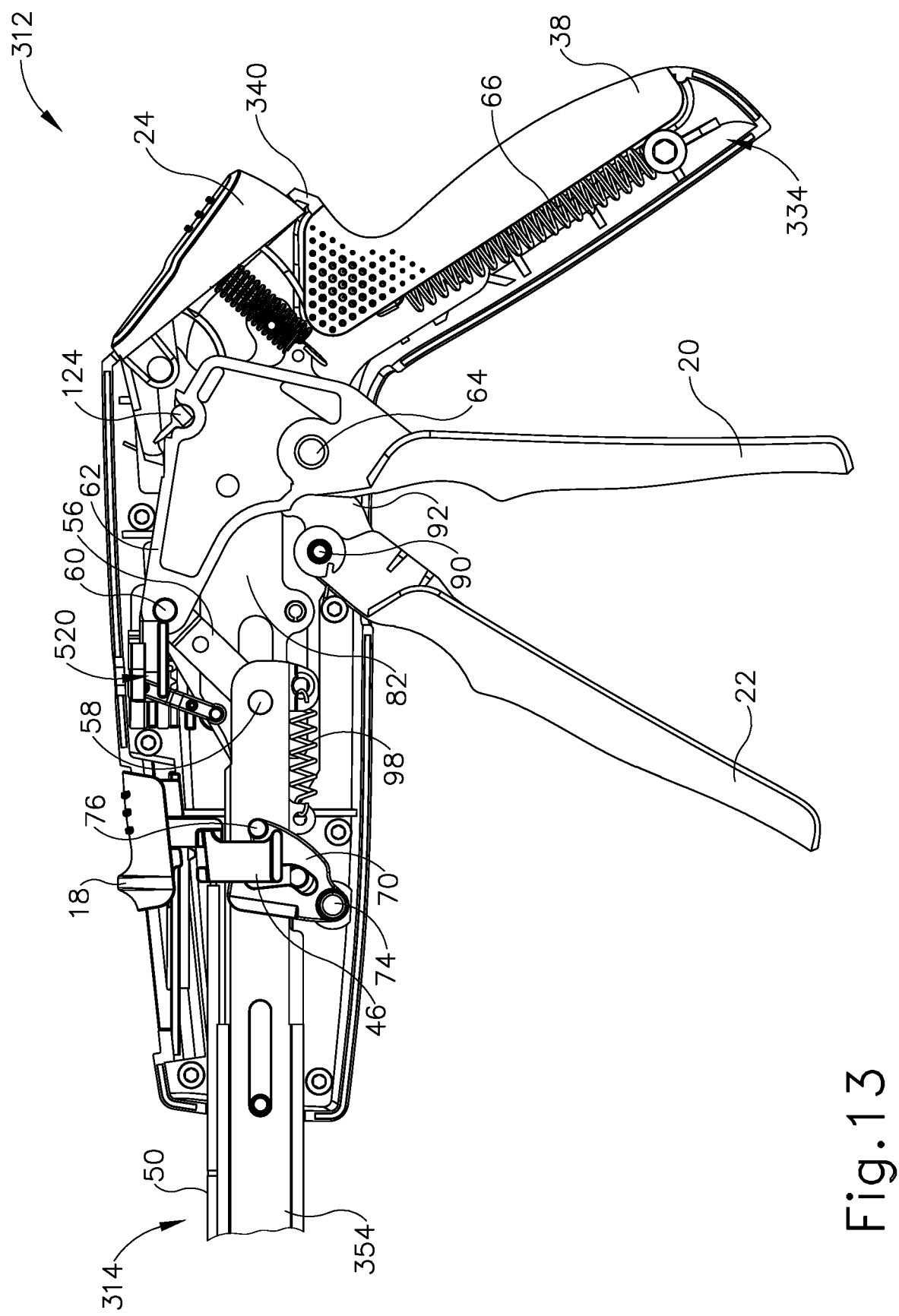
FIG. 13 depicts a right side view of a handle assembly of the surgical stapling instrument of FIG. 12, with various components removed for clarity.

Once fired, the operator may depress release button (24) (see FIG. 2C) and withdraw closure member (54) and firing bar (82) proximally from the actuated, fired position to the unactuated position shown in FIGS. 10A-10B. More particularly, retractor hook (148) engages knife holder (142) to pull knife (32) proximally. At approximately the same time, as cartridge (28) translates proximally with closure member (54), lockout lever (196) of lockout mechanism (131) engages cartridge housing (132) to hold cartridge housing (132) in position. Thereby, the continued pull of knife (32) retracts knife (32) within cartridge housing (132) to inhibit unintended contact by operator with knife (32). Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

It should also be understood that any other components or features of surgical stapling instrument (10) may be configured and operable in accordance with any of the various references cited herein. Additional exemplary modifications that may be provided for surgical stapling instrument (10) will be described in greater detail below. Various suitable ways in which the below teachings may be incorporated into surgical stapling instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to surgical stapling instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Surgical Stapling Instruments with Alternative Handle and Shaft Assemblies While the above surgical stapling instrument (10) provides one example of handle assembly (12) having shaft assembly (14) projecting distally therefrom, it will be appreciated that the operator may desire an alternative handle assembly and/or shaft that may be used with end effector (16) or another, alternative end effector depending on one of a variety particular treatments. For example, likelihood of injury may be decreased with additional communication from surgical stapling instrument (10) to the operator regarding the status of instrument operation. In some versions, the operator manipulates one or both of closure and firing triggers (20, 22) to actuate surgical stapling instrument (10) from the open configuration, to the closured configuration, and further to the fired configuration during use. However, due to the hectic nature of the surgical procedure and/or lack of familiarity with surgical stapling instrument (10), the operator may be become unaware of the particular configuration of end effector (16) positioned within the patient. It may therefore be desirable to provide a surgical stapling instrument (310) with a handle assembly (312, 612, 912) that is configured to communicate or indicate the particular configuration of end effector (16) to the operator during use.

Shaft assembly (314) and handle assemblies (312, 612, 912) are described below in the context of a proctocolectomy surgical procedure. While the following description of shaft and handle assemblies (314, 312, 612, 912) and method of treatment is provided in the context of stapling and/or cutting colon tissue, it will be appreciated that surgical stapling instrument (310) and any of shaft and handle assemblies (314, 312, 612, 912) may be alternatively configured to treat any tissue in the human body with similar features. It should also be understood that the features discussed below may be readily incorporated into surgical stapling instrument (10) discussed above. To this end, like numbers indicate like features described above in greater detail.

A. Exemplary Surgical Stapling Instrument with Feedback Generator

FIGS. 11-14 show surgical stapling instrument (310) with handle assembly (312) and shaft assembly (314) extending distally from handle assembly (312). End effector (316) extends distally from shaft assembly (314) and is configured to fluidly seal and sever tissue with staples (not shown) and knife (32) (see FIG. 6) similar to end effector (14) discussed above in greater detail. To this end, the operator squeezes closure trigger (20) to selectively translate a closure member (354) distally to the closed configuration with tissue captured therein. The operator further squeezes firing trigger (22) to selectively translate firing staples (not shown) and knife (32) (see FIG. 6) from a cartridge (328).

During manipulation of closure and firing triggers (20, 22), a feedback generator (520, 820, 822, 1110, 1112) contained within handle assembly (312) is configured to provide at least one of an audible feedback, a visual feedback, or a tactile feedback to the operator in real time with respect to the operational state or configuration of the surgical stapling instrument (310). For example, surgical stapling instrument (310) may provide feedback when firing trigger (22) fires firing bar (82) a full distal stroke so that the operator may confirm the end of stroke via the feedback.

1. Exemplary Translational Feedback Generator with Audible and Visual Feedback

FIGS. 14-17 show exemplary handle assembly (312) having a translational feedback generator (520) that is configured to generate audible and visual feedback when firing trigger (22) fires firing bar (82) to form staples (not shown) and sever the tissue as discussed above. Translational feedback generator (520) includes a slide feedback assembly (522) supported within a handle housing (334) and adjacent to indicia windows (524), which extend through handle housing (334) for operator view of slide feedback assembly (522) in use. Handle housing (334) also supports a sound generator (526) adjacent to slide feedback assembly (522) such that distal movement of slide feedback assembly (522) causes slide feedback assembly (522) to pluck sound generator (526) to generate an audible click when firing bar (82) is fired. Sound generator (526) may also be configured to temporarily increase resistance to manipulation of firing trigger (22) as sound generator (526) is plucked to further generate tactile feedback to the operator through firing trigger (22).

Figure 14:
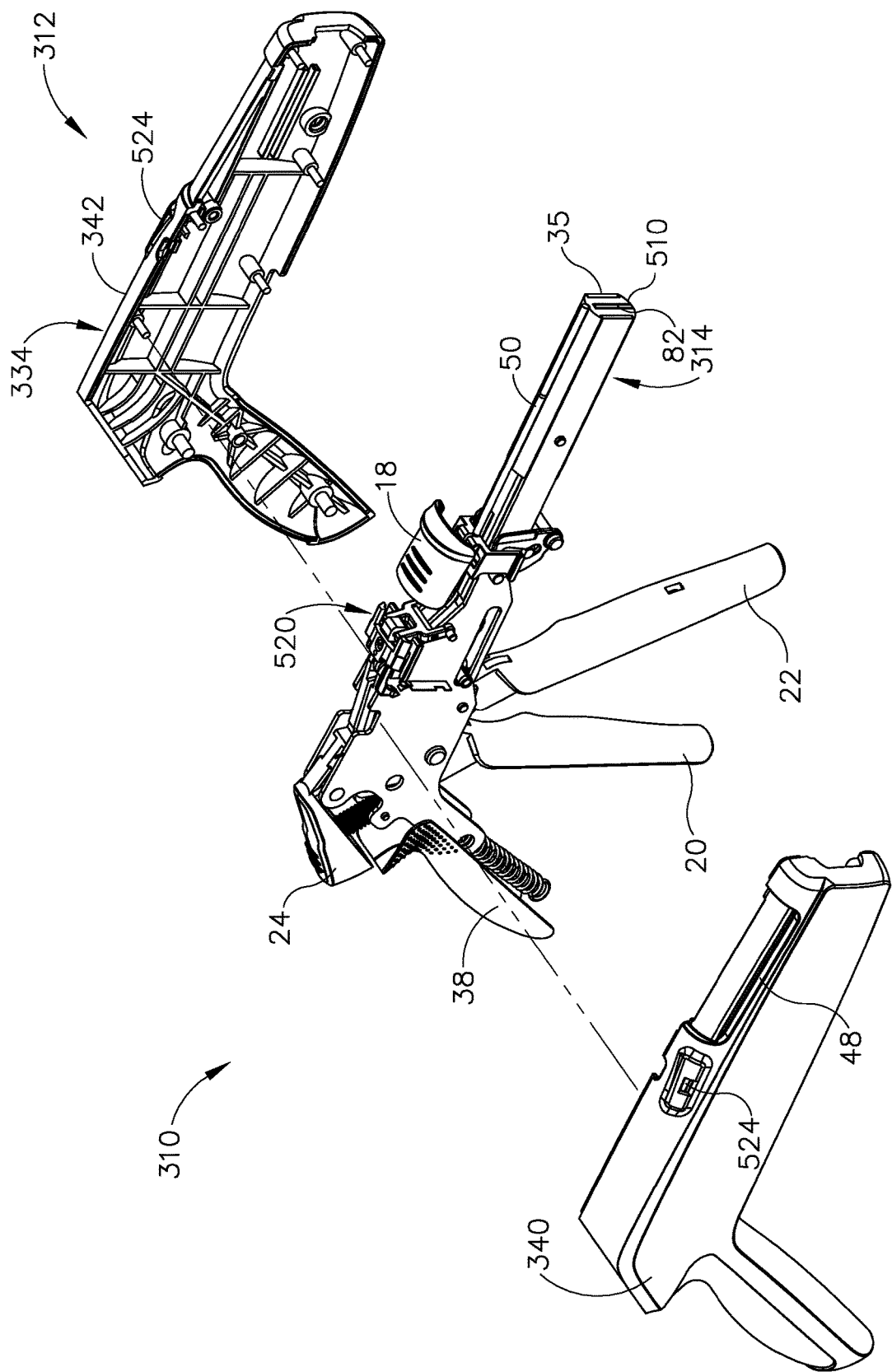
FIG. 14 depicts a partially exploded left front perspective view of a handle assembly of the surgical stapling instrument of FIG. 11, with a left shroud portion and a right shroud portion separated from other components of the handle assembly.
Figure 15:
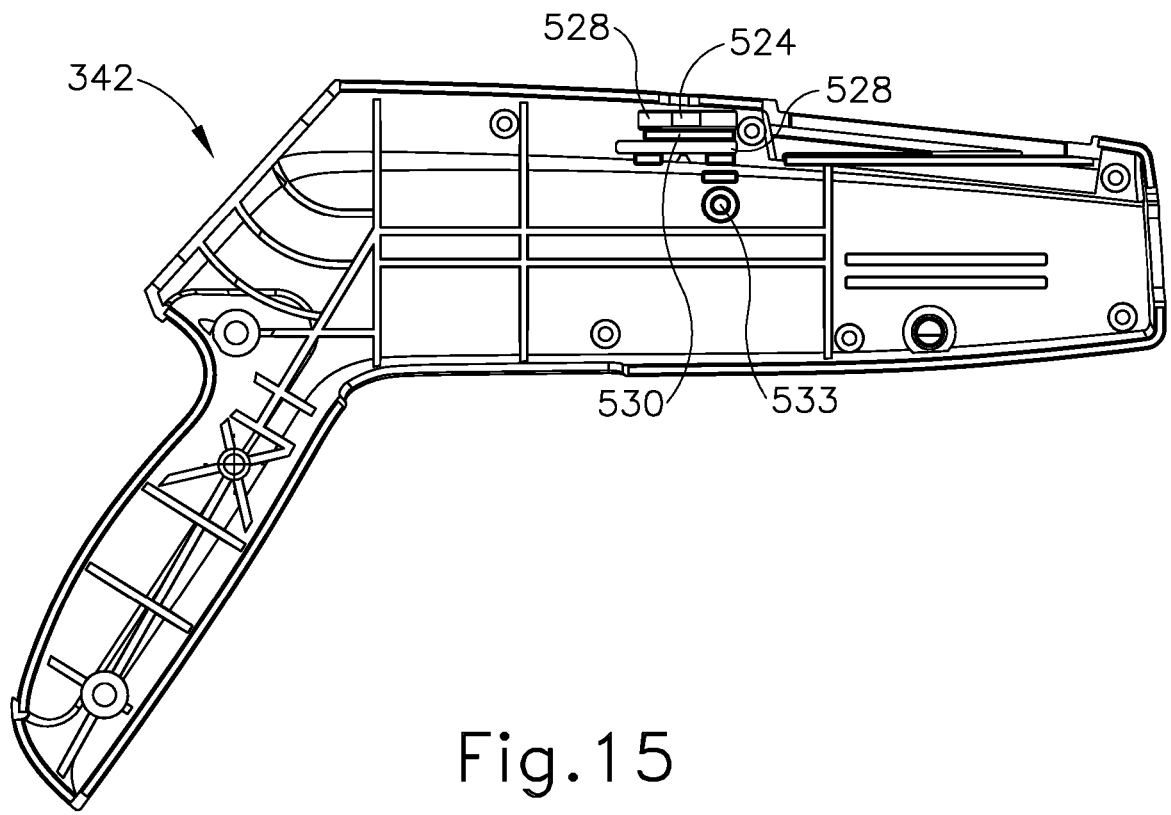
FIG. 15 depicts a left side view of a left shroud portion of the handle assembly of FIG. 14.
Figure 16:
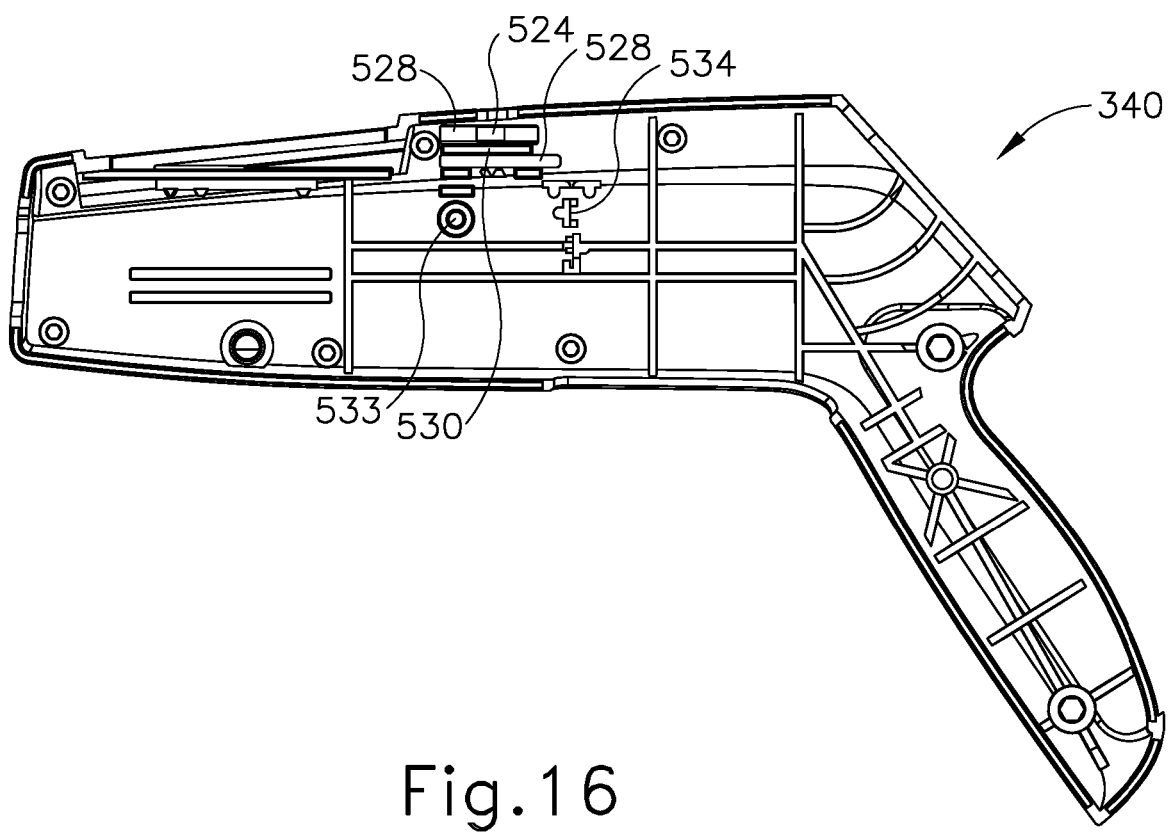
FIG. 16 depicts a right side view of a right shroud portion of the handle assembly of FIG. 14.

FIGS. 14-16 show inner surfaces of left and right shroud handle portions (342, 340) that collectively form handle housing (334) upon assembly. Each shroud handle portion (342, 340) includes a pair of offset support guides (528) extending inwardly to define a pair of slide channels (530) on opposing sides of handle housing (334). Each slide channel (530) slidably receives a lateral end of a sled (532) (see FIG. 17) such that sled (532) (see FIG. 17) is slidably supported between support guides (528). Slide feedback assembly (522) is further connected to mount holes (533) extending inwardly from left and right shroud handle portions (342, 340) and will be discussed below in additional detail. Right shroud handle portion (342) further includes a mounting arrangement (534) in which to secure sound generator (526) (see FIG. 17) adjacent to slide feedback assembly (522). In order to provide viewing of slide feedback assembly (522), each exemplary shroud handle portion (342, 340) includes one indicia window (524) adjacent to a respective support guide (528) for viewing one of a plurality of indicia operatively connected to sled (532) (see FIG. 17) as sled (532) (see FIG. 17) moves along slide channels (530) to indicate whether or not surgical stapling instrument (310) has been fired.

Figure 17:
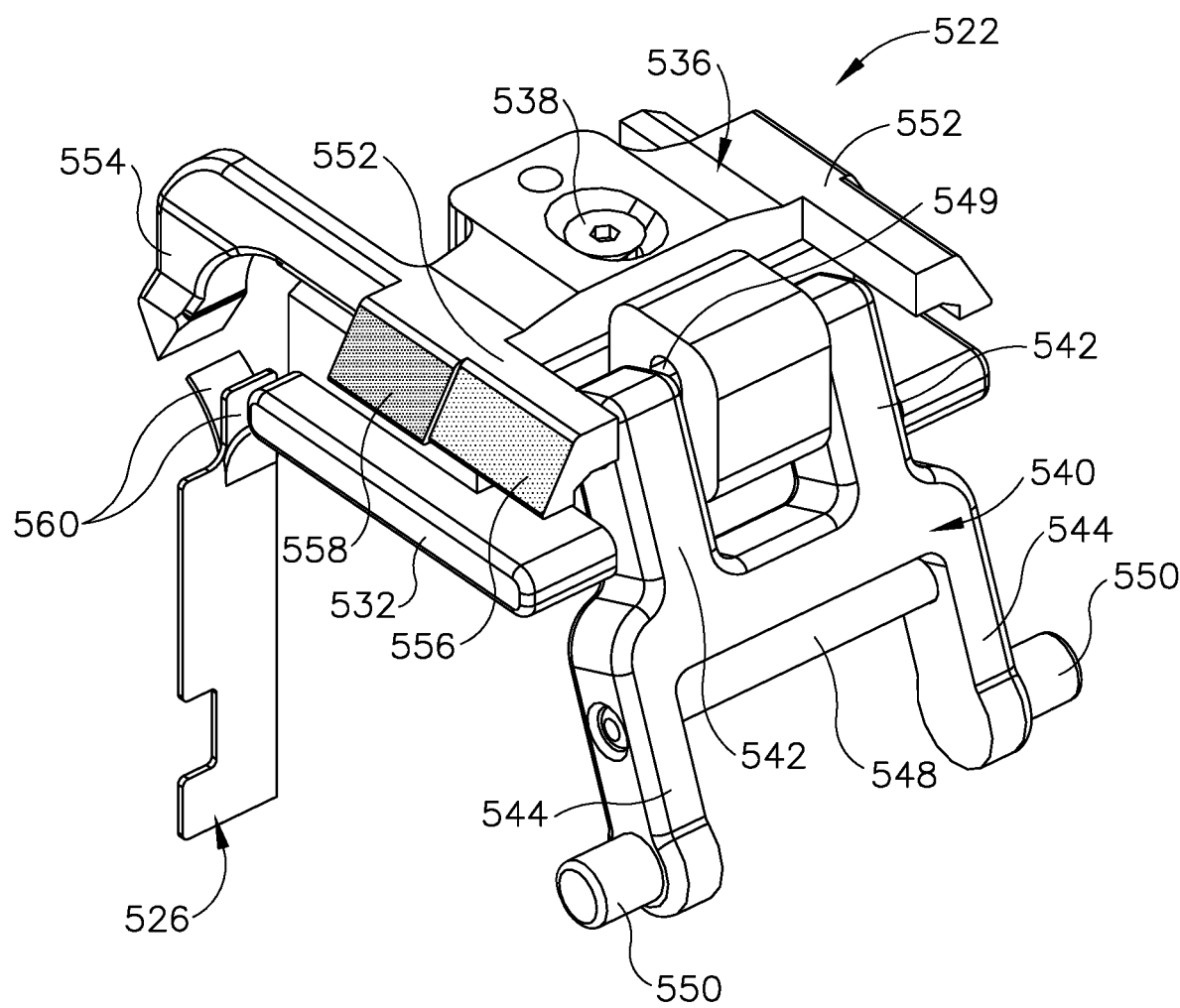
FIG. 17 depicts a left front perspective view of a translational feedback generator of the handle assembly of FIG. 14.
Figure 18:
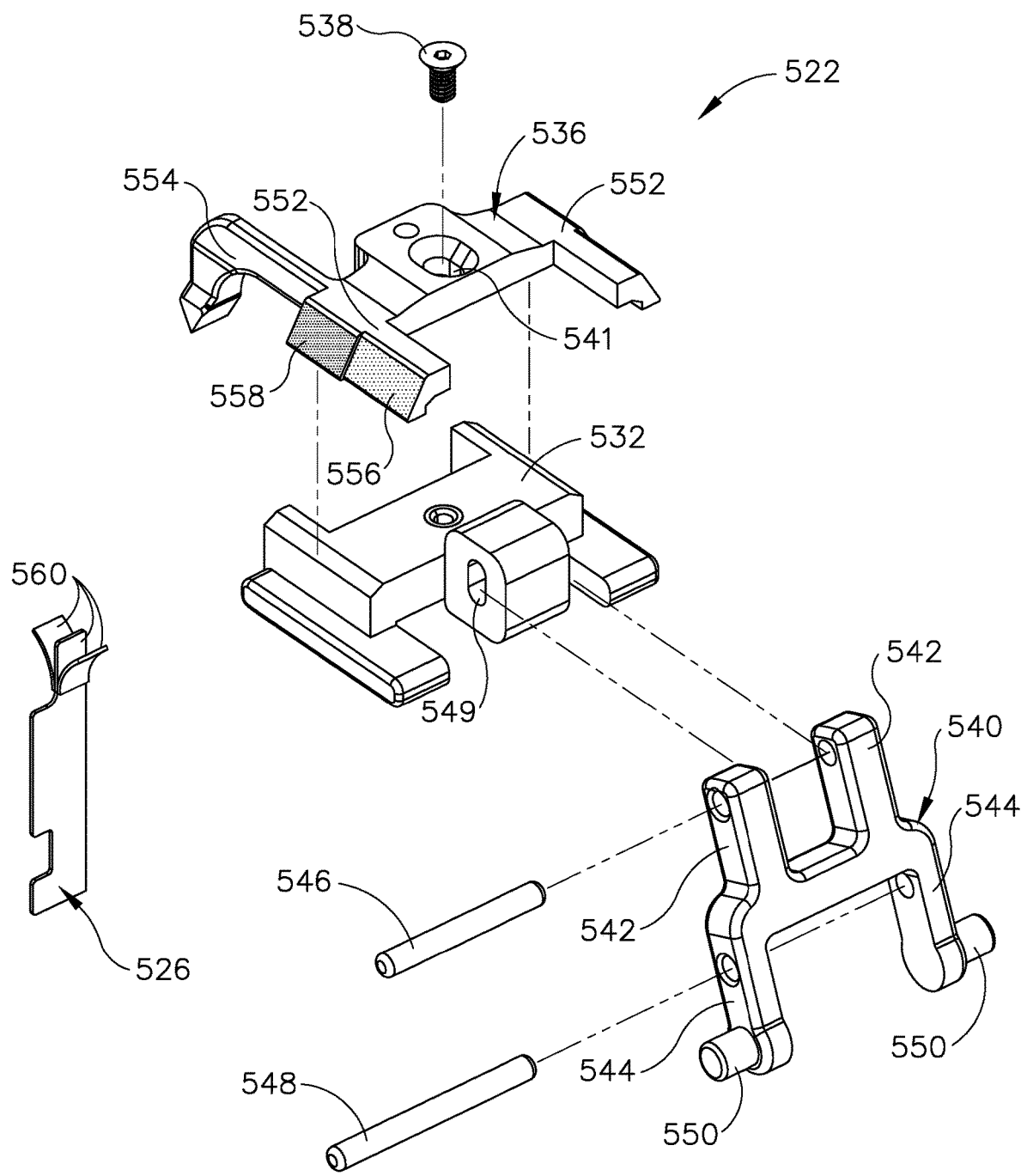
FIG. 18 depicts an exploded left front perspective view of the translational feedback generator of FIG. 17.

Slide feedback assembly (522) and sound generator (526) are shown in greater detail in FIGS. 17 and 18. While sound generator (526) is mounted within handle housing (334) rather than to slide feedback assembly (522), sound generator (526) has been included here for clarity as to the exemplary arrangement of slide feedback assembly (522) relative to sound generator (526). Slide feedback assembly (522) includes sled (532), a feedback member (536) mounted on top of sled (532) via a fastener (538), and a linkage coupling (540). Feedback member (536) and sled (532) are configured to provide for calibration of audible and visual feedback, whereas linkage coupling is configured pull sled (532) with feedback member (536). To this end, feedback member (536) is adjustably mounted to sled (532) via fastener (538) to accommodate manufacturing deviations that may occur in handle and shaft assemblies (312, 314). More particularly, feedback member (536) receives fastener (538) within an elongated hole (541) that extends longitudinally as well as through feedback member (536). Depending on part deviation, the feedback member (536) may be positioned more distally or more proximally relative to sled (532) for calibration such that feedback member (536)

communicates the audible and visual feedback at effectively the same approximate time as completion of the firing stroke.

Linkage coupling (540) is generally H-shaped such that an upper portion has an upper pair of legs (542) extending opposite of a pair of lower legs (544). Upper pair of legs (542) has a shortened dowel (546) spanning between each leg (542), whereas lower pair of legs (544) has an elongated dowel (548) spanning between each leg (544). Shortened dowel (546) pivotally connects linkage coupling (540) to sled (532) via a hole (549) in sled (532). In contrast, elongated dowel (546) provides a catch by which to engage firing bar (82) as described with respect to FIGS. 20A-20C below. Each of the lower pair of legs (544) further includes an outwardly extending pivot pin (550) that is configured to be respectively received within mount holes (533) (see FIGS. 14-15) for pivotally mounting linkage coupling (540) to handle housing (334).

Feedback member (536) includes a pair of proximally extending legs (552) and a distally extending, L-shaped pick (554), which projects toward sound generator (526) to pluck sound generator (526) in use. Each of legs (552) aligns with a respective indicia window (524) and includes an unfired indicia (556) adjacent to a fired indicia (558). Unfired indicia (556) and fired indicia (558) may be viewed by the operator through each indicia window (524) as the operator selectively actuates firing bar (83) from the unfired position to the fired position. In addition, sound generator (526) has a plurality of feedback tabs (560) that are cantilevered upwardly and configured to resonate with audible feedback after being plucked by pick (554).

Linkage coupling (540) is further configured to magnify movement of the unfired and fired indicia (556, 558) relative to firing bar (82) for greater resolution when viewed by the operator through indicia window (524) for improved visibility during use. Exemplary linkage coupling (540) is pivotally mounted about pivot pins (550) such that elongated dowel (548) is a shortened radial distance from pivot pins (550) than shortened dowel (546). In other words, pivotal movement about pivot pins (550) results in shortened dowel (546) moving a greater distance than elongated dowel (546). The movement of sled (532), which is directly connected to shortened dowel (546) will thereby be magnified relative to firing bar (82) and handle housing (334). Thus, relatively small manipulations of firing trigger (22) will result in relatively large movement of unfired and fired indicia (556, 558) within indicia window (524) for greater resolution and improved viewing by the operator.

Figure 19:
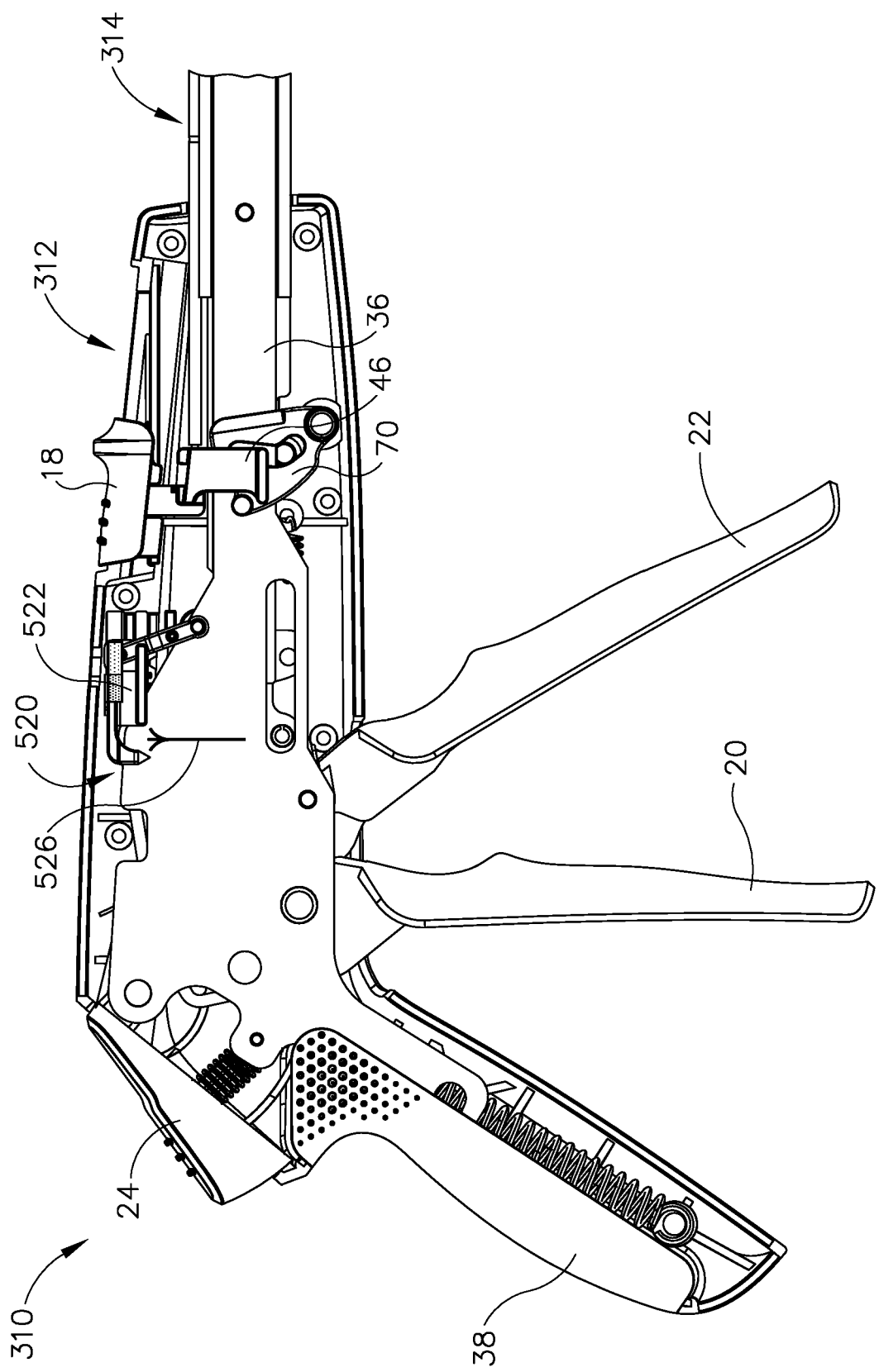
FIG. 19 depicts a left side view of the handle assembly of FIG. 14 with various components removed for clarity.

With respect to FIGS. 19 and 20A, slide feedback assembly (522) is in a relatively distal position within slide channel (530) such that pick (554) is distally positioned from feedback tabs (560) and firing bar (82) is in a relatively distal, unfired position prior to firing firing bar (82). The operator squeezes firing trigger (22) to simultaneously direct firing bar (82) distally toward the fired position. As firing bar (82) translates distally between lower legs (544), a catch element (562) that extends upwardly from firing bar (82) engages elongated dowel (548) as shown in FIG. 20B. Thereby, firing bar (82) distally pivots linkage coupling (540) about pivot pins (550) such that linkage coupling (540) pulls sled (532) distally along slide channels (530). Sled (532) thus carries feedback member (536) distally as pick (554) plucks feedback tabs (560) to audibly indicate to the operator that firing bar (82) has been fired.

Figure 21A:
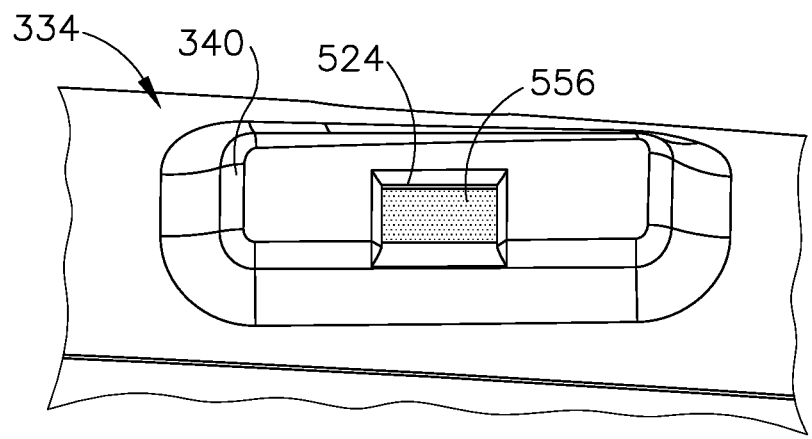
FIG. 21A depicts an enlarged side view of an indicia window of the handle assembly of FIG. 14, with the translational feedback generator in the unfired position.
Figure 21B:
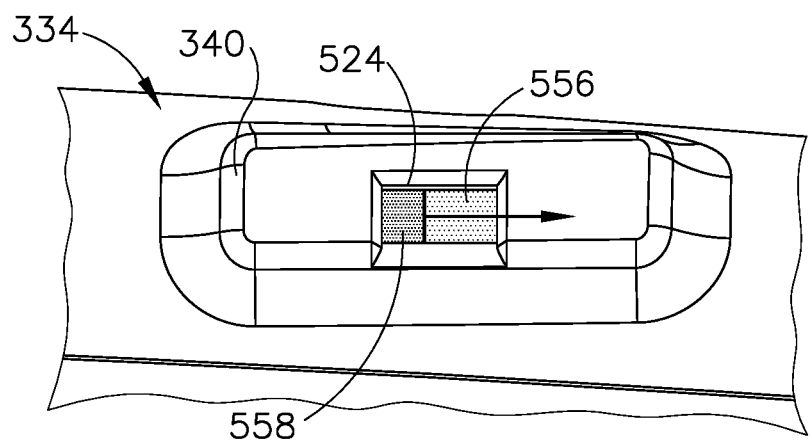
FIG. 21B depicts an enlarged side view of an indicia window of the handle assembly of FIG. 14, with the translational feedback generator moving toward the fired position.
Figure 21C:
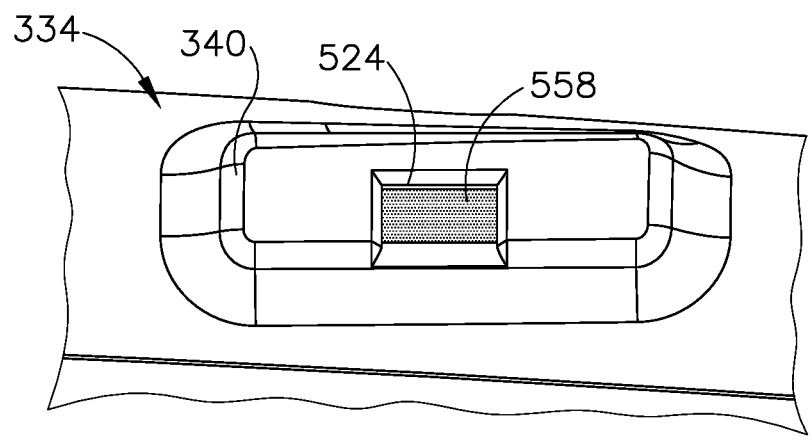
FIG. 21C depicts an enlarged side view of an indicia window of the handle assembly of FIG. 14, with the translational feedback generator in the fired position.

Distal translation of feedback member (536) to indicate firing further translates unfired indicia (556) and fired indicia (558) relative to indicia window (524) as shown in FIGS. 21A-21C. Specifically, FIG. 21A illustrates unfired indicia (556) in alignment with indicia window (524) prior to firing. The operator squeezes firing trigger (22) and, as firing bar (82) fires distally, unfired indicia (556) and fired indicia (558) translate distally as shown in FIG. 21B. Finally, fired indicia (558) aligns with indicia window (524) once firing is complete to indicate to the operator that surgical stapling instrument (310) (see FIG. 11) has been fired.

Figure 22:
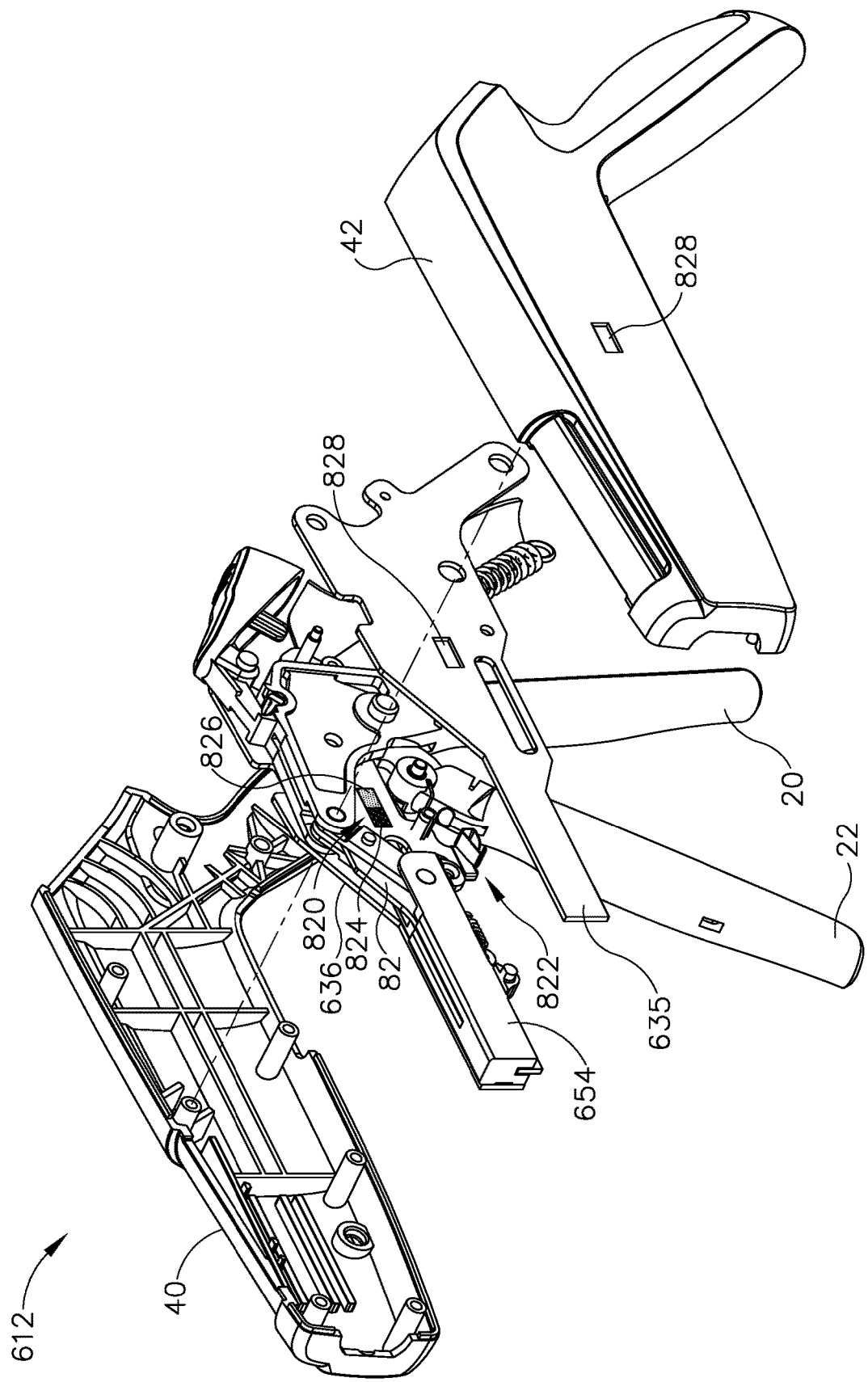
FIG. 22 depicts a partially exploded right front perspective view of a third exemplary handle assembly having a visual feedback generator and an audible feedback generator.

2. Exemplary Translational Visual Feedback Generator and Audible Feedback Generator FIG. 22 shows an exemplary alternative handle assembly (612) that has a visual feedback generator (820) and an audible feedback generator (822). Visual feedback generator (820) includes an unfired indicia (824) positioned distally from and adjacent to a fired indicia (826). Each of unfired indicia (824) and fired indicia (826) are positioned directly on firing bar (82) and move with firing bar (82) to indicate firing to the operator. To enable viewing of indicia (824, 826) on firing bar (82), a pair of indicia windows (828) extend in alignment with indicia (824, 826) through handle frame plate (635) and shroud handle portion (42). Indicia windows (828) align with unfired indicia (824) and fired indicia (826), respectively, in the unfired state such that the operator may view the unfired indicia (824) and fired indicia (826) therethrough. While the particular alignment of indicia (824, 826) and windows (828) may be beneficial for viewing by a right-handed grip of handle assembly (612), it will be appreciated that similar features may be positioned on an opposite side of handle assembly (612) for more easily being viewed by an operator using a left-handed grip.

Figure 24C:
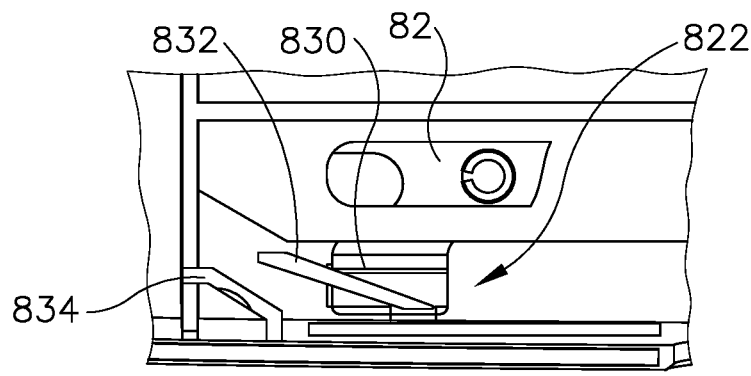
FIG. 24C depicts an enlarged right side view of the audible feedback generator of the handle assembly of FIG. 22, with various components removed for clarity, and with the audible feedback generator moving further toward the fired position.
Figure 24D:
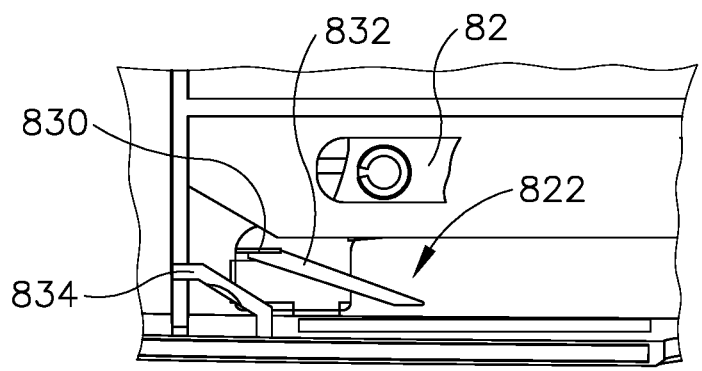
FIG. 24D depicts an enlarged right side view of the audible feedback generator of the handle assembly of FIG. 22, with various components removed for clarity, and with the audible feedback generator moving even further toward the fired position.
Figure 24E:
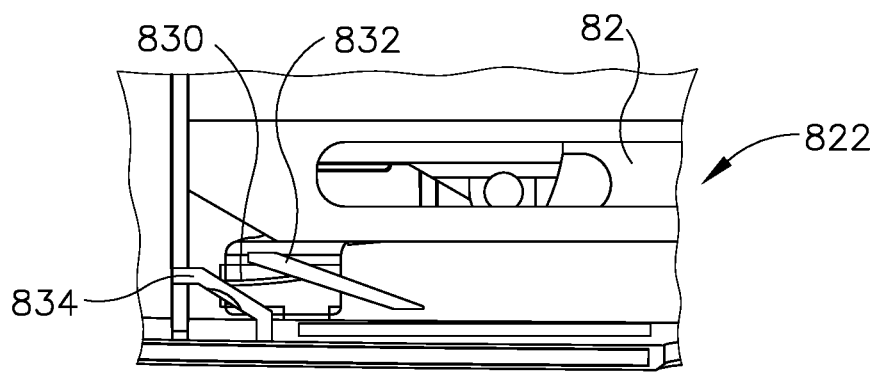
FIG. 24E depicts an enlarged right side view of the audible feedback generator of the handle assembly of FIG. 22, with various components removed for clarity, and with the audible feedback generator in the fired position.
Figure 25A:
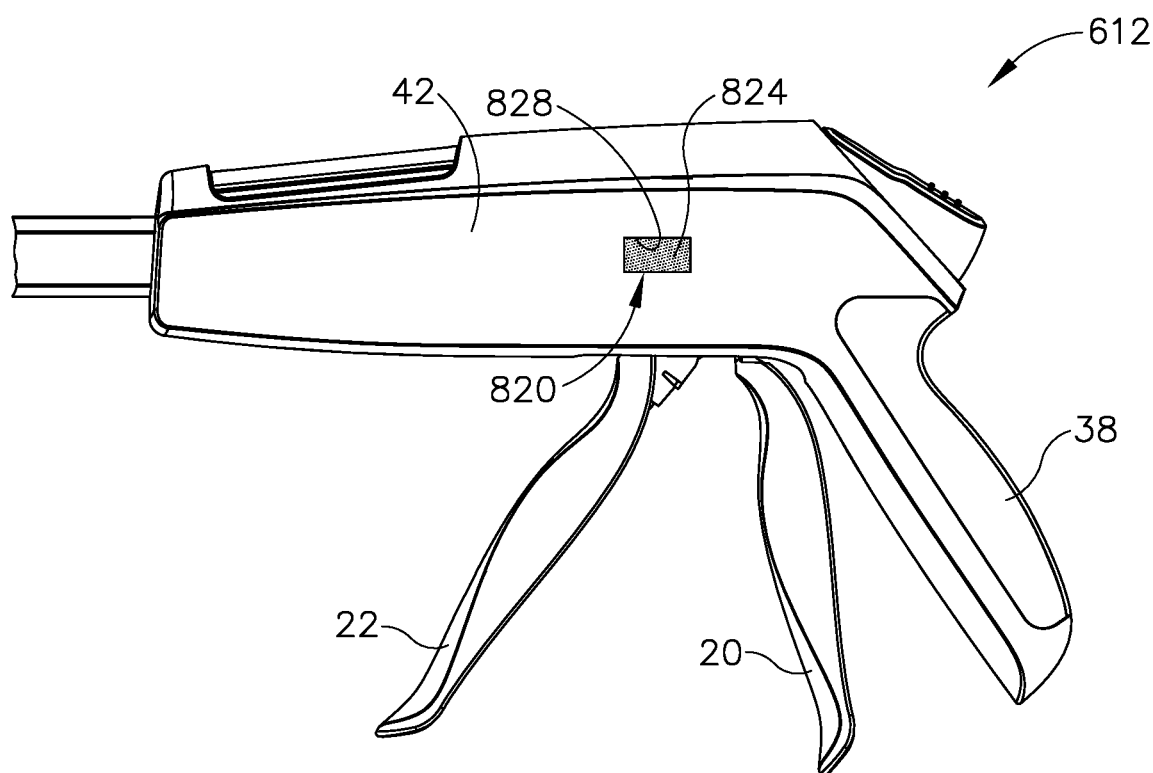
FIG. 25A depicts a side view of the handle assembly of FIG. 22, with the visual feedback generator in the unfired position as viewable through the indicia window of the handle assembly.
Figure 25B:
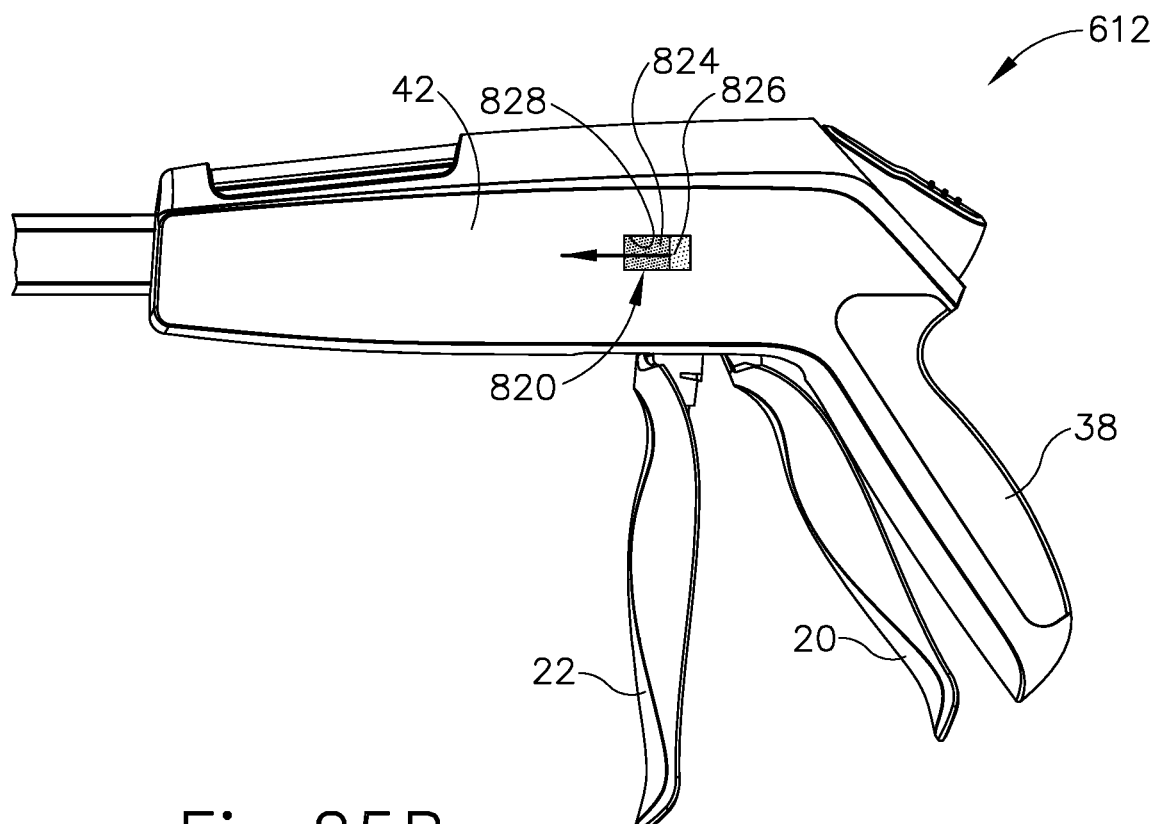
FIG. 25B depicts a side view of the handle assembly of FIG. 22, with the visual feedback generator moving toward the fired position as viewable through the indicia window of the handle assembly.
Figure 25C:
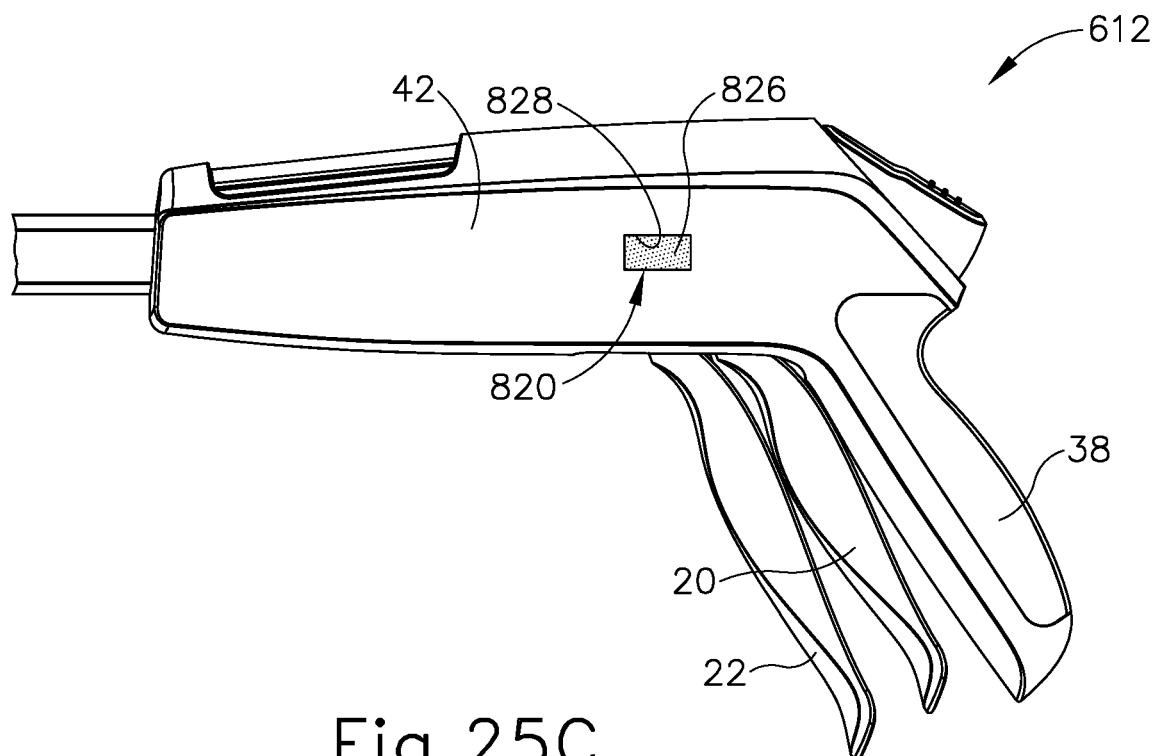
FIG. 25C depicts a side view of the handle assembly of FIG. 22, with the visual feedback generator in the fired position as viewable through the indicia window of the handle assembly.

Audible feedback generator (822) is shown in greater detail in FIGS. 23 and 24A to include a resiliently mounted clip (830) extending from firing bar (82) so as to align with a ramp (832) integrally formed with inner surface of shroud handle portion (42). As shown in succession in FIGS. 24A-24C, firing (actuating) firing bar (82) forces audible feedback generator (822) to translate distally such that clip (830) engages and rises along a top surface of ramp (832). As clip (830) continues to rise along ramp (832), clip (830) is resiliently cocked at top of ramp (832) and continues to be resiliently biased downwardly toward a drum surface (834) in FIG. 24D. Clip (830) continues to translate distally until falling off of ramp (832) and snapping to engage drum surface (834) to generate an audible click. Clip (830) is configured to generate the click as firing bar (82) completes the firing stroke as shown in FIG. 24E. As firing bar (82) moves distally to cock clip (830), unfired indicia (824) and fired indicia (826) move distally as shown in FIGS. 25A-25B. Finally, with firing bar (82) in the fired position, fired indicia (826) is visible to the operator through indicia windows (824) to indicate that the firing bar (82) has effectively been fired during use.

Figure 26:
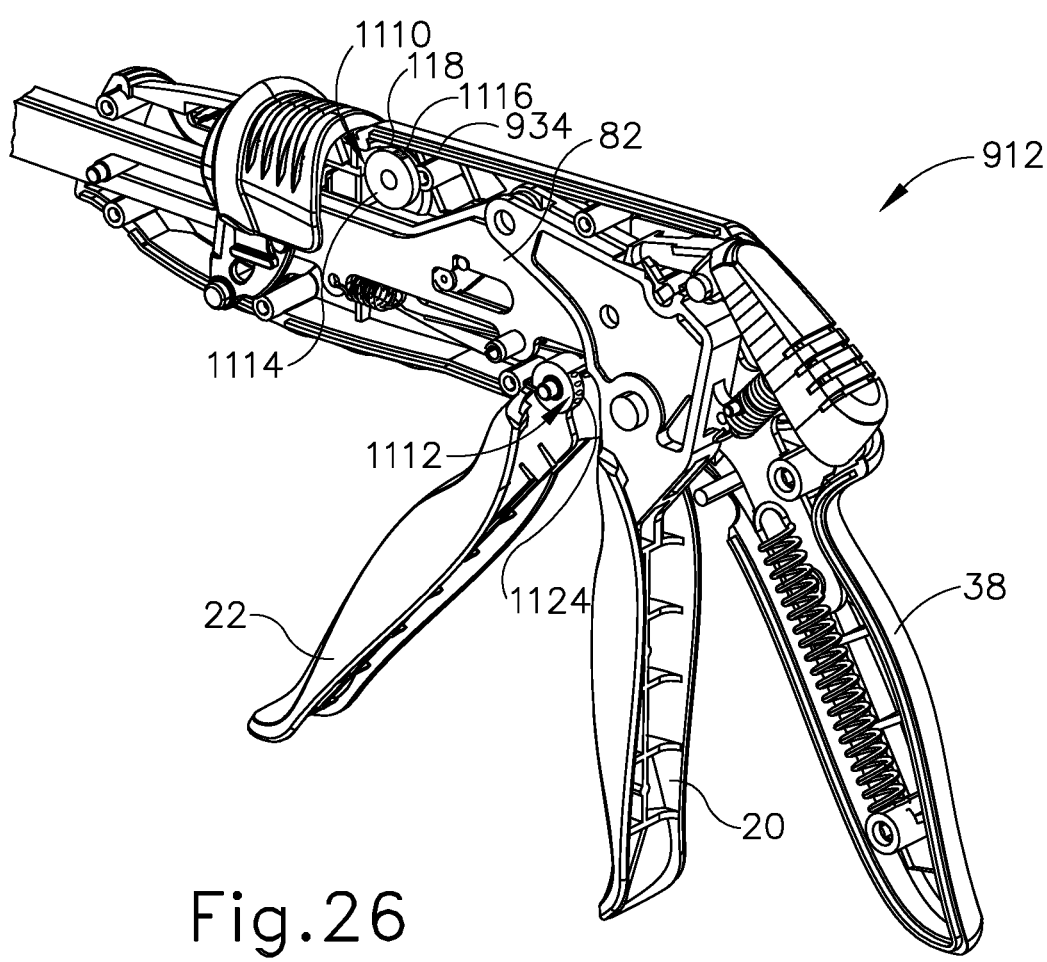
FIG. 26 depicts a rear perspective view of another exemplary handle assembly having a rotational visual feedback generator and a tactile feedback generator with various components removed for clarity.
Figure 27:
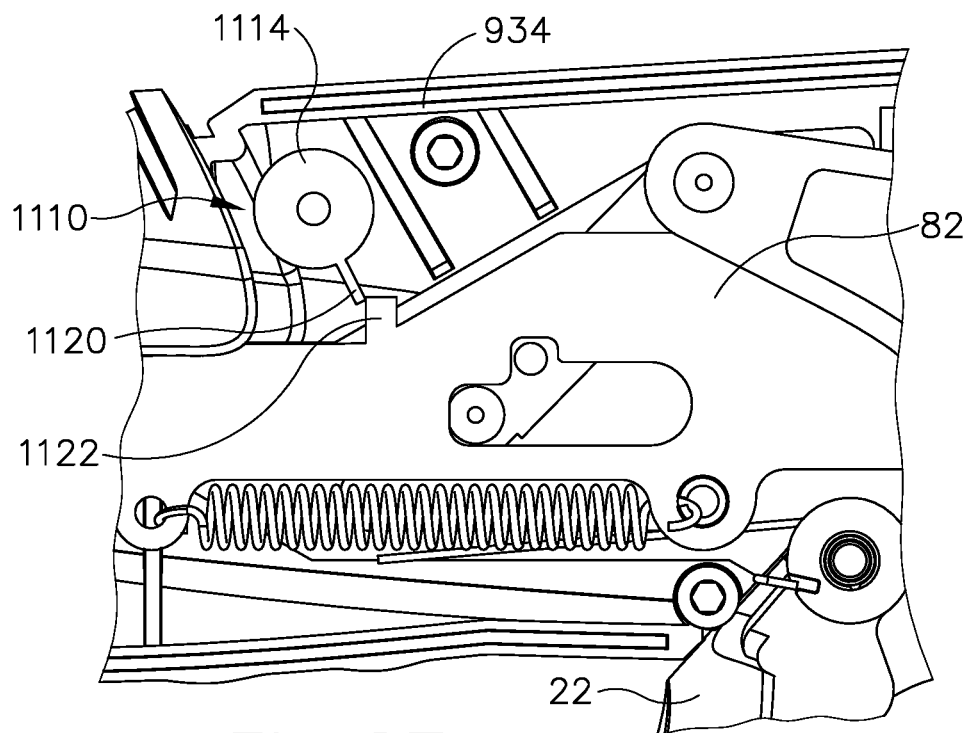
FIG. 27 depicts an enlarged right side view of the rotational visual feedback generator of the handle assembly of FIG. 26.
Figure 28:
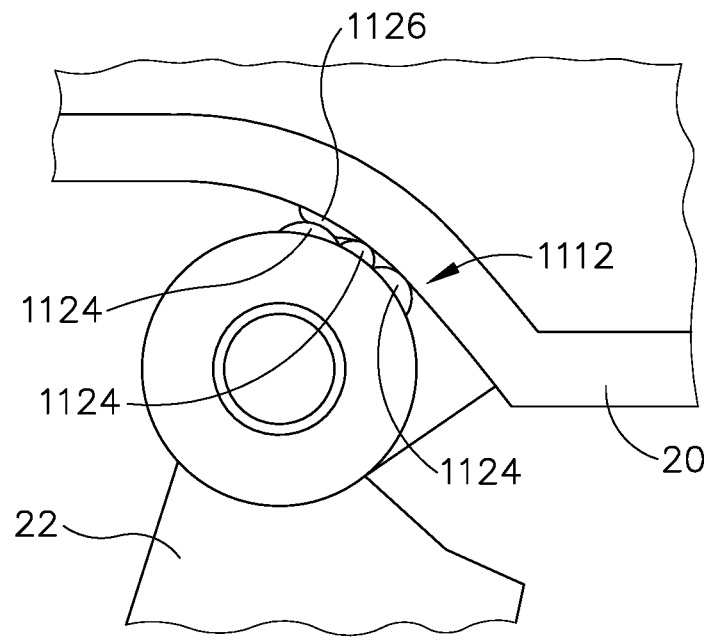
FIG. 28 depicts an enlarged right side view of the tactile feedback generator of the handle assembly of FIG. 26.

3. Exemplary Rotational Visual Feedback Generator and Tactile Feedback Generator FIGS. 26-28 show another exemplary alternative handle assembly (912) that includes a rotational visual feedback generator (1110) and a tactile feedback generator (1112). Rotational visual feedback generator (1110) includes a generally cylindrical wheel (1114) having a peripheral outer surface with an unfired indicia (1116) and a fired indicia (1118). Handle housing (934) includes an indicia window (not shown) adjunct to the peripheral outer surface such that the operator may view the unfired indicia (1116) and fired indicia (1118) during use as discussed above with respect to alternative unfired and fired indicia.

A driven tab (1120) extends radially outwardly from the peripheral outer surface of wheel (1114), whereas a drive tab (1122) extends upwardly from firing bar (82). As shown in FIG. 27, drive tab (1122) is configured to engage driven tab (1120) and rotate wheel (1114) to the fired position and display the fired indicia (1118) through indicia window (not shown) to indicate that firing bar (82) has been fired.

With respect to FIG. 28, tactile feedback generator (1112) includes a plurality of raised bumps (1124, 1126) that rub against each other as firing bar (82) completes the firing stroke. More particularly, closure trigger (20) has at least one raised bump (1126) that is configured to move proximate to firing trigger (22) in the closed configuration. The operator then squeezes firing trigger (22) and the plurality of raised bumps (1124) on firing trigger (22) frictionally rub against the at least one raised bump (1126) to generate a vibration along closure trigger (22). In one example, the plurality of bumps (1124, 1126) is positioned to generate vibration indicative of complete firing of firing bar (82). However, it will be appreciated that the plurality of raised bumps (1124, 1126) may be alternatively positioned on alternative structures to generate tactile feedback indicative of other configurations that may be desirable to the operator.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector receiving a cartridge, the cartridge including at least one of a knife and a plurality of staples and configured to actuate from an unfired cartridge position to a fired cartridge position, wherein the knife is configured to cut tissue when actuated from the unfired cartridge position to the fired cartridge position and the plurality of staples are configured to fasten the tissue when actuated from the unfired cartridge position to the fired cartridge position; (b) a shaft assembly connected to the end effector such that the end effector extends distally from the shaft assembly; and (c) a handle assembly connected to the shaft assembly such that the shaft assembly extends distally from the handle assembly, the handle assembly, including: (i) a handle housing, (ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position when the firing member is actuated through the firing stroke, and (iii) a feedback generator operatively connected to the firing member and configured to communicate an audible sound and a visual indicia to an operator indicative of the firing member completing the firing stroke for actuating the cartridge to the fired cartridge position.

Example 2

The surgical instrument of Example 1, wherein the feedback generator further includes: (A) a sound generator mounted within the handle housing and configured to generate the audible sound, and (B) a feedback assembly movably mounted within the handle housing proximate to the sound generator and configured to be driven from an unfired feedback position to a fired feedback position, wherein the feedback assembly includes the visual indicia thereon, and wherein the feedback assembly is configured to strike the sound generator thereby generating the audible sound as the feedback assembly is driven from the unfired feedback position to the fired feedback position via the firing member actuating the firing stroke.

Example 3

The surgical instrument of Example 2, wherein the firing member includes a catch element, wherein the catch element is configured to engage the feedback assembly as the firing member actuates from the first position to the second position and thereby drive the feedback assembly from the unfired feedback position to the fired feedback position.

Example 4

The surgical instrument of any one or more of Examples 2 through 3, wherein the feedback assembly further includes a sled slidably mounted within the handle assembly and configured to be translatably driven from the unfired feedback position to the fired feedback position.

Example 5

The surgical instrument of Example 4, wherein the feedback assembly further includes a linkage coupling pivotally mounted within the handle assembly and pivotally connected to the sled, wherein the linkage coupling is configured to be engaged by the firing member actuating from the first position to the second position and pull the sled from the unfired feedback position to the fired feedback position, wherein a first distance between the unfired feedback position and the fired feedback position is greater than a second distance between the first position and the second position such that the linkage member is configured to magnify movement of the sled for improving resolution of the visual indicia to the operator.

Example 6

The surgical instrument of any one or more of Examples 2 through 5, further wherein the sound generator further comprises a feedback tab configured to be plucked and cause the sound generator to resonate the audible sound, wherein the feedback assembly further comprises a pick, wherein the pick is configured to pluck the feedback tab as the feedback assembly is driven from the unfired feedback position to the fired feedback position.

Example 7

The surgical instrument of any one or more of Examples 2 through 6, further comprising an indicia window extending through the handle housing and aligned with the visual indicia such that the visual indicia is visible through the indicia window.

Example 8

The surgical instrument of Example 7, wherein the visual indicia includes an unfired visual indicia and a fired visual indicia, wherein the unfired visual indicia is configured to align with the indicia window in the unfired feedback position such that the unfired visual indicia is visible through the indicia window and configured to communicate to the operator that the cartridge is in the unfired cartridge position prior to the firing stroke of the firing member, and wherein the fired visual indicia is configured to align with the indicia window in the unfired feedback position such that the unfired visual indicia is visible through the indicia window and configured to communicate to the operator that the cartridge is in the fired cartridge position after the firing stroke of the firing member.

Example 9

The surgical instrument of any one or more of Examples 2 through 8, wherein the sound generator further comprises a feedback tab configured to be plucked and cause the sound generator to resonate the audible sound, wherein the feedback assembly further comprises a pick extending thereform, wherein the pick is configured to pluck the feedback tab as the feedback assembly is driven from the unfired feedback position to the fired feedback position.

Example 10

The surgical instrument of Example 2, wherein the feedback assembly further includes: (A) a feedback member having the unfired visual indicia and the fired visual indicia thereon and a pick extending therefrom, wherein the pick is configured to strike the sound generator as the feedback assembly is driven from the unfired feedback position to the fired feedback position, and (B) a sled slidably mounted within the handle assembly and configured to be translatably driven from the unfired feedback position to the fired feedback position, and wherein the feedback member is adjustably mounted to the sled assembly such that the position of the feedback member relative to the handle housing is configured to be calibrated to the firing member completing the firing stroke.

Example 11

The surgical instrument of any one or more of Examples 1 through 10, wherein the feedback generator is configured to simultaneously communicate the audible sound and the visual indicia to the operator.

Example 12

The surgical instrument of Example 1, wherein the visual indicia is positioned on the firing member, the surgical instrument further comprising an indicia window extending through the handle housing and aligned with the visual indicia such that the visual indicia is visible through the indicia window.

Example 13

The surgical instrument of Example 1, wherein the feedback generator includes a resilient clip, a ramp, and a drum surface, wherein the resilient clip extends from the firing member and is configured to move with the firing member from an unfired feedback position to a fired feedback position, wherein the ramp is positioned such that the resilient clip is configured to engage the ramp and resiliently bend as the resilient clip moves from the unfired feedback position toward the fired feedback position, and wherein the drum surface is positioned such that the resilient clip is configured to snap from the ramp to the drum surface in the fired position and generate the audible sound therebetween.

Example 14

The surgical instrument of Example 1, the feedback generator having a wheel rotatably mounted within the handle housing, wherein the wheel includes the visual indicia thereon, and wherein the firing member is configured to rotate the firing member from an unfired feedback position to a fired feedback position, the surgical instrument further comprising an indicia window extending through the handle housing and aligned with the visual indicia such that the visual indicia is visible through the indicia window.

Example 15

The surgical instrument of Example 1, further comprising: (a) a first raised bump operatively connected to the firing member; and (b) a second raised bump positioned proximate to the first raised bump, wherein the at first raised bump is configured to grind against the second raised bump and generate the audible sound and a tactile feedback.

Example 16

A surgical instrument comprising: (a) an end effector configured to operatively support a cartridge configured to move from a fired cartridge position to an unfired cartridge position; (b) a shaft assembly connected to the end effector such that the end effector extends distally from the shaft assembly; and (c) a handle assembly connected to the shaft assembly such that the shaft assembly extends distally from the handle assembly, the handle assembly, including: (i) a handle housing, (ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position, and (iii) a feedback generator operatively connected to the firing member and configured to communicate an audible sound and a visual indicia to an operator indicative of the firing member completing the firing stroke for actuating the cartridge to the fired cartridge position.

Example 17

The surgical instrument of Example 16, wherein the feedback generator further includes: (A) a sound generator mounted within the handle housing and configured to generate the audible sound, and (B) a feedback assembly movably mounted within the handle housing proximate to the sound generator and configured to be driven from an unfired feedback position to a fired feedback position, wherein the feedback assembly includes the visual indicia thereon, and wherein the feedback assembly is configured to strike the sound generator thereby generating the audible sound as the feedback assembly is driven from the unfired feedback position to the fired feedback position via the firing member actuating the firing stroke.

Example 18

The surgical instrument of Example 17, wherein the sound generator comprises a feedback tab configured to be plucked and cause the sound generator to resonate the audible sound, wherein the feedback assembly comprises a pick extending therefrom, wherein the pick is configured to pluck the feedback tab as the feedback assembly is driven from the unfired feedback position to the fired feedback position.

Example 19

The surgical instrument of any one or more of Examples 17 through 18, further comprising an indicia window extending through the handle housing and aligned with the visual indicia such that the visual indicia is visible through the indicia window.

Example 20

A method of indicating that a cartridge of a surgical stapling instrument has been fired from an unfired position to a fired position, the method comprising: (a) selectively actuating a firing member a firing stroke from a first position to a second position; (b) actuating a cartridge from an unfired cartridge position to a fired cartridge position via selective actuation of the firing member to the second position; (c) simultaneously generating an audible sound and a visual indicia when the firing member completes the firing stroke to indicate firing of the cartridge to the fired position; and (d) at least one of severing tissue of a patient or fastening the tissue of the patient upon firing the cartridge to the fired position.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

The entire disclosures of: U.S. Pat. No. 5,403,312, entitled "Electrosurgical Hemostatic Device," which issued on Apr. 4, 1995; U.S. Pat. No. 7,000,818, entitled "Surgical Stapling Instrument having Separate Distinct Closing and Firing Systems," which issued on Feb. 21, 2006; U.S. Pat. No. 7,422,139, entitled "Motor-Driven Surgical Cutting and Fastening Instrument with Tactile Position Feedback," which issued on Sep. 9, 2008; U.S. Pat. No. 7,464,849, entitled "Electro-Mechanical Surgical Instrument with Closure System and Anvil Alignment Components," which issued on Dec. 16, 2008; U.S. Pat. No. 7,670,334, entitled "Surgical Instrument Having An Articulating End Effector," which issued on Mar. 2, 2010; U.S. Pat. No. 7,753,245, entitled "Surgical Stapling Instruments," which issued on Jul. 13, 2010 U.S. Pat. No. 8,393,514, entitled "Selectively Orientable Implantable Fastener Cartridge," which issued on Mar. 12, 2013 U.S. patent application Ser. No. 11/343,803, entitled "Surgical Instrument Having Recording Capabilities;" now U.S. Pat. No. 7,845,537; U.S. patent application Ser. No. 12/031,573, entitled "Surgical Cutting And Fastening Instrument Having RF Electrodes," filed Feb. 14, 2008, now abandoned; U.S. patent application Ser. No. 12/031,873, entitled "End Effectors For A Surgical Cutting And Stapling Instrument," filed Feb. 15, 2008, now U.S. Pat. No. 7,980,443; U.S. patent application Ser. No. 12/235,782, entitled "Motor-Driven Surgical Cutting Instrument," now U.S. Pat. No. 8,210,411; U.S. patent application Ser. No.

12/249,117, entitled "Powered Surgical Cutting And Stapling Apparatus With Manually Retractable Firing System," now U.S. Pat. No. 8,608,045; U.S. patent application Ser. No. 12/647,100, entitled "Motor-Driven Surgical Cutting Instrument with Electric Actuator Directional Control Assembly," filed Dec. 24, 2009; now U.S. Pat. No. 8,220,688; U.S. patent application Ser. No. 12/893,461, entitled "Staple Cartridge," filed Sep. 29, 2012, now U.S. Pat. No. 8,733,613; U.S. patent application Ser. No. 13/036,647, entitled "Surgical Stapling Instrument," filed Feb. 28, 2011, now U.S. Pat. No. 8,561,870; U.S. patent application Ser. No. 13/118,241, entitled "Surgical Stapling Instruments With Rotatable Staple Deployment Arrangements," now U.S. Patent Application Publication No. 2012/0298719, issued as U.S. Pat. No. 9,072,535 on Jul. 7, 2015; U.S. patent application Ser. No. 13/524,049, entitled "Articulatable Surgical Instrument Comprising A Firing Drive," filed on Jun. 15, 2012; now U.S. Patent Application Publication No. 2013/0334278, issued as U.S. Pat. No. 9,101,358 on Aug. 11, 2015; U.S. patent application Ser. No. 13/800,025, entitled "Staple Cartridge Tissue Thickness Sensor System," filed on Mar. 13, 2013, now U.S. Patent Application Publication No. 2014/0263551, issued as U.S. Pat. No. 9,345,481 on May 24, 2016; U.S. patent application Ser. No. 13/800,067, entitled "Staple Cartridge Tissue Thickness Sensor System," filed on Mar. 13, 2013, now U.S. Patent Application Publication No. 2014/0263552, now abandoned ; U.S. Patent Application Publication No. 2007/0175955, entitled "Surgical Cutting And Fastening Instrument With Closure Trigger Locking Mechanism," filed Jan. 31, 2006, now abandoned; and U.S. Patent Application Publication No. 2010/0264194, entitled "Surgical Stapling Instrument With An Articulatable End Effector," filed Apr. 22, 2010, now U.S. Pat. No. 8,308,040, are hereby incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising: (a) an end effector receiving a cartridge, the cartridge including at least one of a knife and a plurality of staples and configured to actuate from an unfired cartridge position to a fired cartridge position, wherein the knife is configured to cut tissue when actuated from the unfired cartridge position to the fired cartridge position and the plurality of staples are configured to fasten the tissue when actuated from the unfired cartridge position to the fired cartridge position; (b) a shaft assembly connected to the end effector such that the end effector extends distally from the shaft assembly; and (c) a handle assembly connected to the shaft assembly such that the shaft assembly extends distally from the handle assembly, the handle assembly, including: (i) a handle housing, (ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position when the firing member is actuated through the firing stroke, and (iii) a feedback generator operatively connected to the firing member and configured to communicate an audible sound and a visual indicia to an operator indicative of the firing member completing the firing stroke for actuating the cartridge to the fired cartridge position, wherein the feedback generator further includes: (A) a stationary first audible feedback member fixedly mounted relative to the handle housing, and (B) a feedback assembly configured to be driven from an unfired feedback position to a fired feedback position based on movement of the firing member, the feedback assembly comprising a movable feedback member, wherein the visual indicia is positioned on the movable feedback member such that the visual indicia is movable from the unfired feedback position to the fired feedback position, wherein the movable feedback member further has a second audible feedback member fixed on the movable feedback member and fixed relative to the visual indicia, wherein the second audible feedback member is movable from the unfired feedback position to the fired feedback position, wherein the second audible feedback member is configured to engage the first audible feedback member as the movable feedback member is driven from the unfired feedback position to the fired feedback position and thereby cause the first audible feedback member to emit the audible sound, wherein the feedback assembly further includes a sled and a linkage coupling pivotally mounted within the handle housing and pivotally connected to the sled such that the linkage coupling is fixed to the sled by a first pin.

2. The surgical instrument of claim 1, wherein the second audible feedback member is configured to strike the first audible feedback member thereby generating the audible sound as the feedback assembly is driven from the unfired feedback position to the fired feedback position via the firing member actuating the firing stroke.

3. The surgical instrument of claim 1, wherein the firing member includes a catch element, wherein the catch element is configured to engage the feedback assembly as the firing member actuates from the first position to the second position and thereby drive the feedback assembly from the unfired feedback position to the fired feedback position.

4. The surgical instrument of claim 3, wherein the feedback assembly further includes the sled slidably mounted within the handle housing and configured to be translatably driven from the unfired feedback position to the fired feedback position.

5. The surgical instrument of claim 4, wherein the linkage coupling is configured to be engaged by the firing member actuating from the first position to the second position and pull the sled from the unfired feedback position to the fired feedback position, wherein a first distance between the unfired feedback position and the fired feedback position is greater than a second distance between the first position and the second position such that the linkage member is configured to magnify movement of the sled for improving resolution of the visual indicia to the operator.

6. The surgical instrument of claim 5, wherein the linkage coupling is pivotally connected to the handle housing such that the linkage coupling is fixed to the sled by a second pin.

7. The surgical instrument of claim 1, further wherein the first audible feedback member comprises a feedback tab configured to be plucked and cause the first audible feedback member to resonate the audible sound, wherein the second audible feedback member comprises a pick, wherein the pick is configured to pluck the feedback tab as the feedback assembly is driven from the unfired feedback position to the fired feedback position.

8. The surgical instrument of claim 1, further comprising an indicia window extending through the handle housing and aligned with the visual indicia such that the visual indicia is visible through the indicia window.

9. The surgical instrument of claim 8, wherein the visual indicia includes an unfired visual indicia and a fired visual indicia, wherein the unfired visual indicia is configured to align with the indicia window in the unfired feedback position such that the unfired visual indicia is visible through the indicia window and configured to communicate to the operator that the cartridge is in the unfired cartridge position prior to the firing stroke of the firing member, and wherein the fired visual indicia is configured to align with the indicia window in the unfired feedback position such that the unfired visual indicia is visible through the indicia window and configured to communicate to the operator that the cartridge is in the fired cartridge position after the firing stroke of the firing member.

10. The surgical instrument of claim 1, wherein the feedback assembly further includes the sled slidably mounted within the handle assembly and configured to be translatably driven from the unfired feedback position to the fired feedback position, and wherein the feedback member is adjustably mounted to the sled such that the position of the feedback member relative to the handle housing is configured to be calibrated to the firing member completing the firing stroke.

11. The surgical instrument of claim 10, further comprising a support guide projecting from the handle housing, wherein the support guide slidably supports the sled within the handle housing such that the sled is configured to slide along the support guide.

12. The surgical instrument of claim 1, wherein the feedback generator is configured to simultaneously communicate the audible sound and the visual indicia to the operator.

13. A surgical instrument comprising:
(a) an end effector configured to operatively support a cartridge configured to move from a fired cartridge position to an unfired cartridge position;
(b) a shaft assembly connected to the end effector such that the end effector extends distally from the shaft assembly; and
(c) a handle assembly connected to the shaft assembly such that the shaft assembly extends distally from the handle assembly, the handle assembly, including:
(i) a handle housing,
(ii) a firing member configured to selectively actuate from a first position to a second position as a firing stroke, wherein the firing member is operatively connected to the cartridge via the shaft assembly such that the firing member is configured to actuate the cartridge from the unfired cartridge position to the fired cartridge position, and
(iii) a feedback generator operatively connected to the firing member and configured to communicate an audible sound to an operator indicative of the firing member completing the firing stroke for actuating the cartridge to the fired cartridge position, wherein the feedback generator further includes
(A) a sound generator mounted within the handle housing and secured relative to the handle assembly, wherein the sound generator includes a feedback tab having a first side and an opposing, second side configured to resonate with the audible sound when plucked, and
(B) a feedback assembly including a sled movably mounted within the handle housing proximate to the feedback tab and configured to be driven from an unfired feedback position to a fired feedback position, wherein the feedback assembly includes a linkage coupling and a pick projecting from the sled,
wherein the pick is configured to pluck the feedback tab and pass beyond the first and second sides of the feedback tab as the feedback assembly is driven from the unfired feedback position to the fired feedback position thereby resonating the feedback tab and communicating the audible sound therefrom, and
wherein the linkage coupling is pivotally mounted within the handle housing and pivotally connected to the sled such that the linkage coupling is fixed to the sled by a pin.

14. The surgical instrument of claim 13, wherein the feedback generator further includes a visual indicia configured to indicate to the operator that the firing member completed the firing stroke, and wherein the visual indicia in positioned on the feedback assembly.

15. The surgical instrument of claim 14, further comprising an indicia window extending through the handle housing and aligned with the visual indicia such that the visual indicia is visible through the indicia window.

16. The surgical instrument of claim 14, wherein the feedback assembly further includes a feedback member movably mounted relative to the handle housing, wherein visual indicia is positioned on the feedback member and the pick extends from the feedback member such that the pick and the visual indicia are configured to move relative to the handle housing with the feedback member.

17. The surgical instrument of claim 16, further comprising a support guide projecting from the handle housing, wherein the support guide movably supports the feedback assembly within the handle housing such that the feedback assembly is configured to move relative to the support guide.

18. A method of indicating that a cartridge of a surgical stapling instrument has been fired from an unfired position to a fired position, the method comprising:
(a) selectively actuating a firing member a firing stroke from a first position to a second position, wherein the first position to the second position is a first distance;
(b) actuating a cartridge from an unfired cartridge position to a fired cartridge position via selective actuation of the firing member to the second position;
(c) sliding a sled a having a pick and a visual indicia fixed thereon a second distance based on the first distance, wherein the second distance is greater than the first distance;
(d) plucking a feedback tab with the pick such that the pick passes beyond the feedback tab and the feedback tab resonates an audible sound when the firing member completes the firing stroke;
(e) simultaneously generating the audible sound and a visual indicia when the firing member completes the firing stroke to indicate firing of the cartridge to the fired position; and
(f) at least one of severing tissue of a patient or fastening the tissue of the patient upon firing the cartridge to the fired position.

19. The method of claim 18, wherein the surgical stapling instrument further includes an indicia window, and the method further comprises simultaneously viewing the visual indicia through the indicia window as the firing member completes the firing stroke.

20. The surgical instrument of claim 18, wherein the surgical stapling instrument further includes a linkage coupling engaged with the firing member and pivotally connected to the sled by a pin, the method further comprising moving a first portion of the linkage engaged with the firing member the first distance while simultaneously moving a second portion of the linkage the second distance thereby magnifying the movement of the second portion of the linkage based on the movement of the first portion of the linkage.

\* \* \* \* \*